US012735684B2

(12) United States Patent
Zhou et al.

(10) Patent No.: US 12,735,684 B2
(45) Date of Patent: Sep. 15, 2026

(54) GLYCOSYLTRANSFERASE MUTANT, AND METHOD FOR CATALYTIC SYNTHESIS OF REBAUDIOSIDE M USING GLYCOSYLTRANSFERASE MUTANT

(71) Applicant: XINGHUA GL STEVIA CO., LTD, Xinghua (CN)

(72) Inventors: Boya Zhou, Xinghua (CN); Honghua Jia, Xinghua (CN); Jing Wang, Xinghua (CN); Yan Li, Xinghua (CN); Yehui Tao, Xinghua (CN); Jie Yu, Xinghua (CN); Lei Lin, Xinghua (CN); Ruiqi Ma, Xinghua (CN)

(73) Assignee: XINGHUA GL STEVIA CO., LTD, Xinghua (CN)

( * ) Notice: Subject to any disclaimer, the term of this patent is extended or adjusted under 35 U.S.C. 154(b) by 345 days.

(21) Appl. No.: 18/574,052

(22) PCT Filed: Jul. 29, 2022

(86) PCT No.: PCT/CN2022/109046
§ 371 (c)(1),
(2) Date: Dec. 25, 2023

(87) PCT Pub. No.: WO2023/024828
PCT Pub. Date: Mar. 2, 2023

(65) Prior Publication Data

US 2024/0287479 A1 Aug. 29, 2024

(30) Foreign Application Priority Data

Aug. 23, 2021 (CN) ......................... 202110967784.5

(51) Int. Cl.

| | |
|---|---|
| ***C12N 9/10*** | (2006.01) |
| ***C12N 15/70*** | (2006.01) |
| ***C12P 19/18*** | (2006.01) |

(52) U.S. Cl.
CPC ......... *C12N 9/1051* (2013.01); *C12N 9/1062* (2013.01); *C12N 15/70* (2013.01); *C12P 19/18* (2013.01); *C12Y 204/01* (2013.01)

(58) Field of Classification Search
None
See application file for complete search history.

(56) References Cited

FOREIGN PATENT DOCUMENTS

| | | | |
|---|---|---|---|
| CN | 105051195 | A | 11/2015 |
| CN | 109750072 | * | 5/2019 |

(Continued)

OTHER PUBLICATIONS

Ho et al., Process Biochemistry 41: 1829-1834 (2006).*

(Continued)

*Primary Examiner* — Erin M. Bowers
(74) *Attorney, Agent, or Firm* — Bayramoglu Law Offices LLC

(57) ABSTRACT

A glycosyltransferase mutant and a method for catalytic synthesis of rebaudioside M using the glycosyltransferase mutant are provided. The glycosyltransferase mutant is obtained through mutation based on a glycosyltransferase amino acid sequence shown in SEQ ID NO: 1, and can be produced by inducing expression in a mutant strain. The glycosyltransferase mutant can be used as a catalyst for enzymatic catalytic synthesis of 12.8 g/LRebM from 20 g/LRebE. Michaelis constants (a kinetic parameter) of the glycosyltransferase mutant S195Q for rebaudioside E and rebaudioside D are 56.34±2.02 μM and 214.48±14.54 μM, respectively, which are ⅓ and ⅖ of a Michaelis constant of a wild-type (WT) glycosyltransferase, respectively. The glycosyltransferase mutant can be coupled with sucrose synthase (SuSy) to allow the catalytic synthesis of rebaudioside M and a recombinant strain in which a glycosyltransferase UGT76G1 or a mutant thereof is co-expressed (Continued)

with SuSy is constructed to allow the catalytic synthesis of rebaudioside M.

6 Claims, 4 Drawing Sheets

Specification includes a Sequence Listing.

(56) References Cited

FOREIGN PATENT DOCUMENTS

| | | | |
|---|---|---|---|
| CN | 109750072 | A | 5/2019 |
| CN | 112080480 | * | 12/2020 |
| CN | 112080480 | A | 12/2020 |
| CN | 112375750 | A | 2/2021 |
| CN | 113462670 | A | 10/2021 |
| WO | 2020249138 | A1 | 12/2020 |
| WO | WO 2020/249138 | * | 12/2020 |

OTHER PUBLICATIONS

Jie Yu, et al., Mutation of Stevia glycosyltransferase UGT76GI for efficient biotransformation of rebaudioside E into rebaudioside M, Journal of Functional Foods, 2022, pp. 1-9, vol. 92, 105033.

Ting Yang, et al., Hydrophobic recognition allows the glycosyltransferase UGT76G1 to catalyze its substrate in two orientations, Nature Communications, 2019, pp. 1-38, vol. 3214 No. 3214.

* cited by examiner 1.4
1.2
1.0
0.8
0.6
0.4
0.2
0.0
Rebaudioside M (g/L)
UGT76G1-StSUS1 UGT76G1-McSuSy S195Q-StSUS1 S195Q-McSuSy
Mutations

GLYCOSYLTRANSFERASE MUTANT, AND METHOD FOR CATALYTIC SYNTHESIS OF REBAUDIOSIDE M USING GLYCOSYLTRANSFERASE MUTANT

CROSS REFERENCE TO THE RELATED APPLICATIONS

This application is the national phase entry of International Application No. PCT/CN2022/109046, filed on Jul. 29, 2022, which is based upon and claims priority to Chinese Patent Application No. 202110967784.5, filed on Aug. 23, 2021, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBXHHC002-PKG_Sequence_Listing.xml, created on 11/29/2023, and is 54,476 bytes in size.

TECHNICAL FIELD

The present disclosure belongs to the technical field of bioengineering, and specifically relates to a method for catalytic synthesis of rebaudioside M using a glycosyltransferase mutant.

BACKGROUND

Steviol glycosides (SGs) are diterpenoids with diterpenoid steviol as a basic backbone. SGs mainly exist in *Stevia rebaudiana* leaves. *Stevia rebaudiana* leaves include a variety of natural SGs such as stevioside, rebaudioside A, rebaudioside B, rebaudioside D, rebaudioside E, and rebaudioside M, among which the rebaudioside M exists in dry leaves at a very low content, but has excellent sweetness and taste. The rebaudioside M is currently recognized as the most desirable SG product. As a novel natural sweetener, the rebaudioside M derived from *Stevia rebaudiana* has advantages such as high sweetness and low calories. However, there are few studies on the synthesis of rebaudioside M.

Glycosyltransferases are mainly found in plants, and can catalyze the transfer of glycosyl to different acceptor molecules to allow glycosylation to produce corresponding glycoside compounds. Glycosyltransferases can be classified as Leloir glycosyltransferases and non-Leloir glycosyltransferases according to different types of glycosyl donors. Glycosyltransferases for catalyzing the synthesis of SGs are mainly uridine diphosphate glycosyltransferases (UGTs). The glycosyltransferase UGT76G1 derived from *Stevia rebaudiana* is a Leloir glycosyltransferase, and is mainly dependent on the glycosyl donor of uridine diphosphate glucose (UDPG). UGT76G1 has excellent substrate promiscuity, which is mainly due to the fact that a receptor binding pocket in the crystal structure of UGT76G1 is relatively large and can accommodate a variety of glycosyl acceptor molecules. UGT76G1 can not only catalyze the synthesis of various SGs, but also catalyze the synthesis of curcumin glycosides from curcumin.

An enzyme molecule can be modified based on a directed evolution theory to obtain an enzyme molecule with improved catalytic efficiency. Analysis of the relationship between structural characteristics and functions of an enzyme is the premise and basis for effective molecular modification of the enzyme. A spatial structure of a protein is first acquired, and then a simulated docking experiment between a known or predicted protein structure and a ligand can be conducted to obtain a complex model of the enzyme and the ligand. Based on a rational design of a protein structure, an active site is found through analysis of the protein structure and mutated, where the active site has an impact on the function of the entire protein and the binding of the protein to a ligand.

Glycosyl donors are indispensable for glycosylation, and major glycosyl donors include UDPG, uridine diphosphate-galactose (UDP-Gal), and uridine diphosphate-glucuronic acid (UDP-GlcA). UDPG is the most widely used, but UDPG has a high price and is not suitable for large-scale applications in industrial production. A coupling reaction of sucrose synthase (SuSy) and glycosyltransferase enables the in-situ regenerative cycle of UDPG by adding sucrose during glycosylation. When a double-enzyme coupling system is established with SuSy and glycosyltransferase to allow double-enzyme catalysis, sucrose cleavage is first catalyzed by the SuSy to produce UDPG and fructose, and then glycosylation is catalyzed by the glycosyltransferase. Uridine diphosphate (UDP) generated during glycosylation can be used by SuSy and converted into UDPG once again, which allows the recycling of UDP and avoids inhibition from accumulation of UDP on enzymatic activity. When a double-enzyme coupling system is adopted, only inexpensive sucrose needs to be used as a substrate instead of expensive UDPG, and thus the production cost can be controlled.

A double-enzyme catalytic system composed of the glycosyltransferase UGT76G1 and SuSy can catalyze the synthesis of an intermediate product, rebaudioside D, from a substrate, rebaudioside E, and then catalyze the synthesis of rebaudioside M from rebaudioside D. Because the intermediate product rebaudioside D has a large molecular weight and poor water solubility, the catalysis of the wild-type (WT) enzyme UGT76G1 for the synthesis of rebaudioside M from rebaudioside E has low efficiency. As a result, the glycosyltransferase UGT76G1 needs to undergo molecular modification to improve the catalytic efficiency of the glycosyltransferase.

SUMMARY

An objective of the present disclosure is to modify the glycosyltransferase UGT76G1 to obtain a UGT76G1 mutant with improved catalytic efficiency for synthesis of rebaudioside M, and provide a method for catalytic synthesis of rebaudioside M using the glycosyltransferase mutant to solve the problem that the current synthesis of rebaudioside M under enzymatic catalysis has a low yield.

To achieve the above objective, the present disclosure adopts the following technical solutions:

A glycosyltransferase mutant for synthesizing rebaudioside M is provided. An amino acid sequence of a glycosyltransferase UGT76G1 is shown in SEQ ID NO: 1. The glycosyltransferase mutant is G87D, S147D, S147N, S195Q, L200Y, T284S, S285W, or G378P.

The G87D is obtained through a mutation of an amino acid at position 87 in the amino acid sequence shown in SEQ ID NO: 1 from glycine (G) to aspartic acid (D);

- the S147D is obtained through a mutation of an amino acid at position 147 in the amino acid sequence shown in SEQ ID NO: 1 from serine (S) to aspartic acid (D);

the S147N is obtained through a mutation of an amino acid at position 147 in the amino acid sequence shown in SEQ ID NO: 1 from serine (S) to asparagine (N);

the S195Q is obtained through a mutation of an amino acid at position 195 in the amino acid sequence shown in SEQ ID NO: 1 from serine (S) to glutamine (Q);

the L200Y is obtained through a mutation of an amino acid at position 200 in the amino acid sequence shown in SEQ ID NO: 1 from leucine (L) to tyrosine (Y);

the T284S is obtained through a mutation of an amino acid at position 284 in the amino acid sequence shown in SEQ ID NO: 1 from threonine (T) to serine (S);

the S285W is obtained through a mutation of an amino acid at position 285 in the amino acid sequence shown in SEQ ID NO: 1 from serine (S) to tryptophan (W); and the G378P is obtained through a mutation of an amino acid at position 378 in the amino acid sequence shown in SEQ ID NO: 1 from glycine (G) to proline (P).

The mutants G87D, S147D, S147N, S195Q, L200Y, T284S, S285W, and G378P are obtained through single-point mutations of the glycosyltransferase UGT76G1.

An expression gene encoding the glycosyltransferase mutant described above is provided.

A recombinant plasmid carrying coding genes for the glycosyltransferase UGT76G1 mutant and SuSy is provided.

The SuSy is StSUS1 or McSuSy.

A recombinant strain is provided, where the recombinant strain is obtained by transforming the recombinant plasmid synthesized above into *Escherichia coli* (*E. coli*) BL21 (DE3).

A method for synthesizing rebaudioside M using a glycosyltransferase mutant is provided, including the following steps:

1) cloning a coding gene for a glycosyltransferase UGT76G1 mutant and a coding gene for SuSy into an expression vector to obtain a corresponding recombinant plasmid;
2) transforming the recombinant plasmid into *E. coli* BL21 (DE3) to obtain a recombinant strain in which the glycosyltransferase mutant and the SuSy are co-expressed;
3) inoculating the recombinant strain into an Luria-Bertani (LB) liquid medium, and adding an inducer to induce expression; centrifuging a resulting bacterial solution at a low temperature, collecting a resulting bacterial precipitate, and resuspending the bacterial precipitate with an appropriate buffer; and subjecting a resulting bacterial suspension to ultrasonication, centrifuging a resulting ultrasonication system, and collecting a resulting supernatant, which is a crude enzyme solution; and
4) adding rebaudioside E or rebaudioside D as a substrate, sucrose, and the crude enzyme solution to a catalytic reaction system, and allowing a reaction at an appropriate temperature; and collecting a sample, inactivating the sample at a high temperature, centrifuging the sample, and collecting a resulting supernatant, which is the rebaudioside M.

An amino acid sequence of the glycosyltransferase UGT76G1 is shown in SEQ ID NO: 1, and a nucleotide sequence for the glycosyltransferase UGT76G1 is shown in SEQ ID NO: 2; a nucleotide sequence for the StSUS1 is shown in SEQ ID NO: 11; and a nucleotide sequence for the McSuSy is shown in SEQ ID NO: 12.

A nucleotide sequence for the mutant G87D of the glycosyltransferase UGT76G1 is shown in SEQ ID NO: 3; a nucleotide sequence for the mutant S147D of the glycosyltransferase UGT76G1 is shown in SEQ ID NO: 4; a nucleotide sequence for the mutant S147N of the glycosyltransferase UGT76G1 is shown in SEQ ID NO: 5; a nucleotide sequence for the mutant S195Q of the glycosyltransferase UGT76G1 is shown in SEQ ID NO: 6; a nucleotide sequence for the mutant L200Y of the glycosyltransferase UGT76G1 is shown in SEQ ID NO: 7; a nucleotide sequence for the mutant T284S of the glycosyltransferase UGT76G1 is shown in SEQ ID NO: 8: a nucleotide sequence for the mutant S285S of the glycosyltransferase UGT76G1 is shown in SEQ ID NO: 9; and a nucleotide sequence for the mutant G378P of the glycosyltransferase UGT76G1 is shown in SEQ ID NO: 10.

The inducer is isopropyl-β-D-thiogalactoside (IPTG), the inducer is added at a concentration of 0.1 mM to 1.0 mM, and the expression is induced for 20 h to 40 h.

In the catalytic reaction system, a concentration of the rebaudioside E is 10 g/L to 50 g/L, a concentration of the sucrose is 10 g/L to 200 g/L, and a concentration of a crude enzyme is 1 g/L to 5 g/L; and the reaction is conducted at 20° C. to 50° C. for 2 h to 32 h.

In the catalytic reaction system, a concentration of the rebaudioside D is 1 g/L to 5 g/L, a concentration of the sucrose is 1 g/L to 20 g/L, and a concentration of a crude enzyme is 1 g/L to 5 g/L; and the reaction is conducted at 20° C. to 50° C. for 2 h to 32 h.

The SuSy is StSUS1 or McSuSy, where a nucleotide sequence for the StSUS1 is shown in SEQ ID NO: 11 and a nucleotide sequence for the McSuSy is shown in SEQ ID NO: 12.

Preferably, the mutant S195Q of the glycosyltransferase UGT76G1 is co-expressed with McSuSy.

Further preferably, a method for catalytic synthesis of rebaudioside M from rebaudioside E using the glycosyltransferase mutant S195Q is provided, including the following steps:

1) cloning a coding gene for a glycosyltransferase UGT76G1 mutant S195Q and a coding gene for McSuSy into an expression vector to obtain a corresponding recombinant plasmid;
2) transforming the recombinant plasmid into *E. coli* BL21 (DE3) to obtain a recombinant strain in which the glycosyltransferase mutant and the McSuSy are co-expressed;
3) inoculating the recombinant strain into an LB liquid medium, and adding an inducer to induce expression; centrifuging a resulting bacterial solution at a low temperature, collecting a resulting bacterial precipitate, and resuspending the bacterial precipitate with an appropriate buffer; and subjecting a resulting bacterial suspension to ultrasonication, centrifuging a resulting ultrasonication system, and collecting a resulting supernatant, which is a crude enzyme solution; and
4) adding the rebaudioside E, sucrose, and the crude enzyme solution to a catalytic reaction system, and allowing a reaction at an appropriate temperature; and collecting a sample, inactivating the sample at a high temperature, centrifuging the sample, and collecting a resulting supernatant, which is the rebaudioside M.

Further preferably, a method for catalytic synthesis of rebaudioside M from rebaudioside D using the glycosyltransferase mutant S195Q is provided, including the following steps:

1) cloning a coding gene for a glycosyltransferase UGT76G1 mutant S195Q and a coding gene for McSuSy into an expression vector to obtain a corresponding recombinant plasmid;

2) transforming the recombinant plasmid into *E. coli* BL21 (DE3) to obtain a recombinant strain in which the glycosyltransferase mutant and the McSuSy are co-expressed;

3) inoculating the recombinant strain into an LB liquid medium, and adding an inducer to induce expression; centrifuging a resulting bacterial solution at a low temperature, collecting a resulting bacterial precipitate, and resuspending the bacterial precipitate with an appropriate buffer; and subjecting a resulting bacterial suspension to ultrasonication, centrifuging a resulting ultrasonication system, and collecting a resulting supernatant, which is a crude enzyme solution; and 4) adding the rebaudioside D, sucrose, and the crude enzyme solution to a catalytic reaction system, and allowing a reaction at an appropriate temperature; and collecting a sample, inactivating the sample at a high temperature, centrifuging the sample, and collecting a resulting supernatant, which is the rebaudioside M.

In the present disclosure, the glycosyltransferase UGT76G1 is subjected to molecular modification. A crystal structure is selected and docked with RebE to obtain a complex model, and single-point mutations are conducted for amino acid residues surrounding RebE in this model. The mutants G87D, S147D, S147N, S195Q, L200Y, T284S, S285W, and G378P are screened out, where the mutants G87D, S195Q, L200Y, T284S, and S285W are preferred, S195Q and L200Y are more preferred, and S195Q is most preferred; and an enzyme activity of S195Q increases by 1.3 times compared with an enzyme activity of the WT glycosyltransferase.

Michaelis constants of the WT glycosyltransferase UGT76G1 to rebaudioside E and rebaudioside D are 170.13±12.61 μM and 478.12±33.03 μM, respectively, and corresponding $K_{cat}/K_m$ values are 11.76 $s^{-1}$ $mM^{-1}$ and 0.42 $s^{-1}$ $mM^{-1}$, respectively; and Michaelis constants of the mutant S195Q to rebaudioside E and rebaudioside D are 56.34±2.02 sM and 214.48±14.54 μM, respectively, and corresponding $K_{cat}/K_m$ values are 26.27 $s^{-1}$ $mM^{-1}$ and 1.17 $s^{-1}$ $mM^{-1}$, respectively. Compared with the WT glycosyltransferase, affinities of the mutant S195Q of the present disclosure for the substrates rebaudioside E and rebaudioside D are improved by 3.0 times and 2.2 times, respectively, and catalytic efficiencies of the mutant S195Q of the present disclosure for the substrates rebaudioside E and rebaudioside D are improved by 2.2 times and 2.8 times, respectively. According to the kinetic parameter data, the mutant S195Q can easily bind to rebaudioside E and rebaudioside D, which is conducive to the catalytic synthesis of rebaudioside M, and will lay an excellent foundation for industrialization of the glycosyltransferase and application of the glycosyltransferase in the food industry.

In the catalytic reaction system, a concentration of the rebaudioside E is 10 g/L to 50 g/L, a concentration of the sucrose is 10 g/L to 200 g/L, and a concentration of the crude enzyme is 1 g/L to 5 g/L; the reaction is conducted at 20° C. to 50° C. and preferably 40° C. for 2 h to 32 h; and in the catalytic reaction system, an optimal concentration of the crude enzyme is 5 mg/mL and an optimal concentration ratio of Reb E to sucrose is 1:5.

BENEFICIAL EFFECTS

In the present disclosure, molecular modification is conducted for the glycosyltransferase UGT76G1 by a directed evolution method to improve an enzyme activity and catalytic efficiency of the enzyme, and a resulting glycosyltransferase mutant can be used to allow the efficient catalytic synthesis of rebaudioside M. The present disclosure provides a guiding method for modification of the glycosyltransferase, which involves simple operations and can lead to a glycosyltransferase mutant with high catalytic efficiency. The glycosyltransferase mutant can improve a yield of rebaudioside M when used in enzymatic synthesis of rebaudioside M, and exhibits improved affinities and catalytic efficiencies for the substrates rebaudioside E and rebaudioside D.

DETAILED DESCRIPTION OF THE EMBODIMENTS

Figure 1:
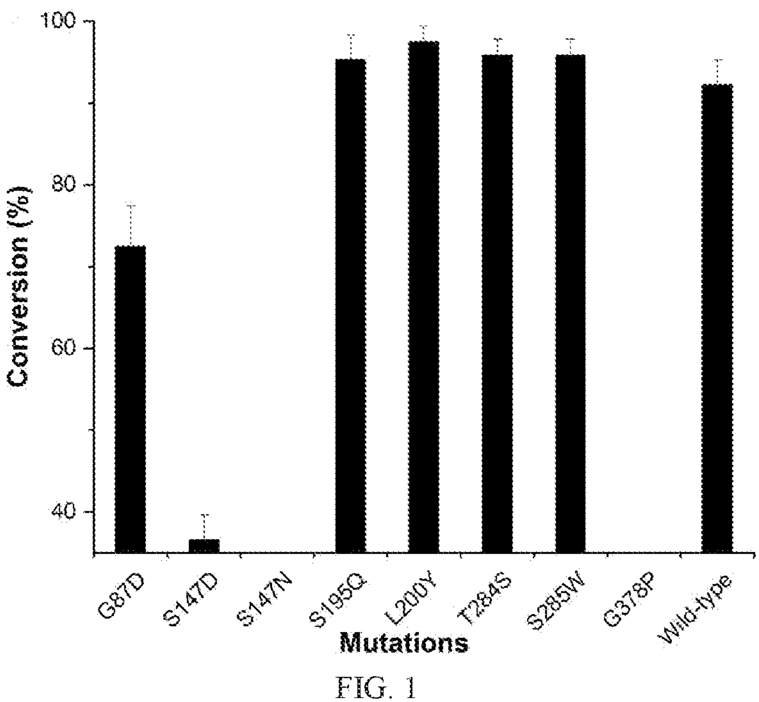
FIG. 1 shows the conversion of recombinases for RebE.

The technical solutions of the present disclosure will be further described below with reference to examples, but the protection scope of the present disclosure is not limited thereto.

Example 1 Screening of Mutants of a Glycosyltransferase UGT76G1

The glycosyltransferase was modified based on a directed evolution theory. A crystal structure was selected and docked with RebE to obtain a complex model, and single-point mutations were conducted for amino acid residues surrounding RebE in this model. A distance between NE2 of a key residue His25 of an active center and an O atom of a C13 glycoside of the substrate RebE in the model was measured. Resulting mutants were ranked according to affinity values. Based on the affinity and distance, the mutants G87D, S147D, S147N, S195Q, L200Y, T284S, S285W, and G378P were screened out, as shown in Table 1.

TABLE 1

Affinity data of the mutants

| Mutant | Affinity(kcal/mol) | Distance(Å) | Autodock Score | vdw | dsolv | tors |
|---|---|---|---|---|---|---|
| S285W | −9.409 | 3.139 | −4.0531 | −17.78 | 6.960 | 8.054 |
| G378P | −9.300 | 3.128 | −4.2975 | −17.68 | 6.812 | 8.054 |
| G87D | −9.265 | 3.273 | −4.1608 | −17.84 | 7.436 | 8.054 |
| S195Q | −9.212 | 3.193 | −3.739 | −17.44 | 7.221 | 8.054 |
| L200Y | −9.198 | 3.151 | −3.7651 | −17.69 | 7.300 | 8.054 |
| S147D | −9.171 | 3.172 | −3.8477 | −17.32 | 7.175 | 8.054 |

TABLE 1-continued

| Affinity data of the mutants | | | | | | |
|---|---|---|---|---|---|---|
| Mutant | Affinity(kcal/mol) | Distance(Å) | Autodock Score | vdw | dsolv | tors |
| S147N | −9.166 | 3.185 | −4.3159 | −17.35 | 7.155 | 8.054 |
| T284S | −9.165 | 3.154 | −3.7613 | −16.91 | 7.141 | 8.054 |

Notes:
Affinity represents a binding affinity; Distance represents a distance between atoms; and vdw represents a van der Waals force.

Example 2 Construction of a Double Enzyme-Expressing System

A double gene-expressing vector pRSFDuet-1 was selected; a nucleotide sequence shown in SEQ ID NO: 2 for a *Stevia rebaudiana*-derived glycosyltransferase UGT76G1 was inserted at a NdeI/XhoI site of the vector; then a nucleotide sequence shown in SEQ ID NO: 11 or 12 for StSUS1 or McSuSy was inserted at a NcoI/EcoRI site of the vector to produce two corresponding recombinant expression plasmids; and the two recombinant plasmids each were transformed into *E. coli* BL21 (DE3) to obtain two recombinant strains co-expressing the two enzymes.

Example 3 Preparation of Mutants of a Glycosyltransferase UGT76G1

A polymerase chain reaction (PCR) amplification technology was used to conduct base-directed mutations with a WT UGT76G1-StSUS1 recombinant plasmid as template DNA.

Primers for a base-directed mutation to produce G87D:

a forward primer: 5'-CCGCTGGCG_ACATGCGTATTCCGATTATCAACGAA-3' (underlined characters represent mutant bases), as shown in SEQ ID NO: 13; and a reverse primer: 5'-AATACGCATICGCCAGCGGGCCGTGGGTCGGCAG-3' (underlined characters represent mutant bases), as shown in SEQ ID NO: 14.

Primers for a base-directed mutation to produce S147D:

a forward primer: 5'-CTGATGACCQ_ACAGCCTGTTCAATTTTCATGCCCAC-3' (underlined characters represent mutant bases), as shown in SEQ ID NO: 15; and a reverse primer: 5'-GAACAGGCTICGGTCATCAGGACCAGGCGACGCAG-3' (underlined characters represent mutant bases), as shown in SEQ ID NO: 16.

Primers for a base-directed mutation to produce S147N:

a forward primer: 5'-CTGATGACCAACAGCCTGTTCAATTTTCATGCCCAC-3' (underlined characters represent mutant bases), as shown in SEQ ID NO: 17; and a reverse primer: 5'-GAACAGGCTaIUGGTCATCAGGACCAGGCGACGCAG-3' (underlined characters represent mutant bases), as shown in SEQ ID NO: 18.

Primers for a base-directed mutation to produce S195Q:

a forward primer: 5'-TCAGCGTACCAAAACTGGCAGATTCTGAAAGAAATC-3' (underlined characters represent mutant bases), as shown in SEQ ID NO: 19; and a reverse primer: 5'-CTGCCAGTTTIQGTACGCTGACTTAATATCCTTGAC-3' (underlined characters represent mutant bases), as shown in SEQ ID NO: 20.

Primers for a base-directed mutation to produce L200Y:

a forward primer: 5'-TGGCAGATTIACAAAGAAATCCTGGGTAAAATGATT-3' (underlined characters represent mutant bases), as shown in SEQ ID NO: 21; and a reverse primer: 5'-GATTTCTTTTAAATCTGCCAGTTCGAGTACGCTGA-3' (underlined characters represent mutant bases), as shown in SEQ ID NO: 22.

Primers for a base-directed mutation to produce T284S:

a forward primer: 5'-TTCGGTAGTAOCTCGGAAGTGGATGAAAAGGACTTT-3' (underlined characters represent mutant bases), as shown in SEQ ID NO: 23, and a reverse primer: 5'-CACTTCCGAGCTACTACCGAAGCTAACATACAGCAC-3' (underlined characters represent mutant bases), as shown in SEQ ID NO: 24.

Primers for a base-directed mutation to produce S285W:

a forward primer: 5'-GGTAGTACCTGGGAAGTGGATGAAAAGGACTTTCTG-3' (underlined characters represent mutant bases), as shown in SEQ ID NO: 25; and a reverse primer: 5'-ATCCACTTCCCAGGTACTACCGAAGCTAACATACAG-3' (underlined characters represent mutant bases), as shown in SEQ ID NO: 26.

Primers for a base-directed mutation to produce G378P:

a forward primer: 5'-TCAGATTTTCCACTGGACCAGCCGCTGAATGCACGT-3' (underlined characters represent mutant bases), as shown in SEQ ID NO: 27; and a reverse primer: 5'-CTGGTCCAGICQAAAATCTGAGAAAATCATCGGGAC-3' (underlined characters represent mutant bases), as shown in SEQ ID NO: 28.

A 50 μL PCR amplification system was as follows: 10 μM forward and reverse primers: each 2 μL; dNTPMix: 1 μL; 2×MaxBuffer: 25 μL; template plasmid: 1 μL; 2 U/50 μL Super-Fidelity DNA polymerase: 1 sL; and sterilized water $ddH_2O$: the balance.

PCR amplification conditions were as follows: pre-denaturation at 95° C. for 30 s; 30 cycles (denaturation at 95° C. for 15 s; annealing at 65° C. for 15 s; and extension at 72° C. for 7 min); thorough extension at 72° C. for 5 min; and finally, holding a temperature of 16° C. A PCR amplification product was tested by agarose gel nucleic acid electrophoresis.

1 μL of DpnI was added to a mutant PCR amplification product, then a resulting reaction system was placed at 37° C. to allow a constant-temperature reaction for 1 h to 2 h and then added to an *E. coli* BL21 (DE3) competent cell, and a resulting mixture was placed on an ice for 30 min, then subjected to a heat shock at 42° C. for 45 s to 90 s, and then placed on an ice for 2 min: 600 μL of an LB medium (formula: NaCl: 10 g/L, yeast powder: 5 g/L, and peptone: 10 g/L) was added, and a resulting bacterial solution was shaken on a shaker at 37° C. and 200 rpm for 45 min, then totally coated evenly on a kanamycin-resistant LB plate, and cultivated overnight at 37° C.; 2 single colonies were picked from the plate, inoculated into an LB liquid medium (formula: NaCl: 10 g/L, yeast powder: 5 g/L, and peptone: 10 g/L), and cultivated for 9 h; a resulting bacterial solution was stored in glycerin-filled tubes and subjected to sequencing, and bacteria with a correct sequencing result in a glycerin-filled tube were coated on a kanamycin-resistant LB plate (formula: NaCl: 10 g/L, yeast powder: 5 g/L, peptone: 10 g/L, and agar: 20 g/L); and mutant recombinant plasmids were extracted from corresponding bacteria, and the mutant recombinant plasmids and a WT recombinant plasmid each were transformed into *E. coli* BL21 (DE3) to obtain corresponding recombinant strains G87D-StSUS1, S147D-StSUS1, S147N-StSUS1, S195Q-StSUS1, L200Y-StSUS1, T284S-StSUS1, S285W-StSUS1, and G378P-StSUS1 and a WT strain UGT76G1-StSUS1.

A PCR amplification technology was used to conduct a base-directed mutation with a WT UGT76G1-McSuSy recombinant plasmid as template DNA.

Primers for a base-directed mutation to produce S195Q:

a forward primer: 5'-TCAGCGTACCAAAACTGGCAGATTCTGAAAGAAATC-3' (underlined characters represent mutant bases), as shown in SEQ ID NO: 19; and a reverse primer: 5'-CTGCCAGTTTT_GTACGCTGACTTAATATCCTTGAC-3' (underlined characters represent mutant bases), as shown in SEQ ID NO: 20.

A 50 μL PCR amplification system was as follows: 10 μM forward and reverse primers: each 2 μL; dNTPMix: 1 μL; 2×MaxBuffer: 25 μL; template plasmid: 1 μL; 2 U/50 μL Super-Fidelity DNA polymerase: 1 sL; and sterilized water $ddH_2O$: the balance.

PCR amplification conditions were as follows: pre-denaturation at 95° C. for 30 s; 30 cycles (denaturation at 95° C. for 15 s; annealing at 65° C. for 15 s, and extension at 72° C. for 7 min); thorough extension at 72° C. for 5 min; and finally, holding a temperature of 16° C. A PCR amplification product was tested by agarose gel nucleic acid electrophoresis.

1 μL of DpnI was added to a mutant PCR amplification product, then a resulting reaction system was placed at 37° C. to allow a constant-temperature reaction for 1 h to 2 h and then added to an *E. coli* BL21 (DE3) competent cell, and a resulting mixture was placed on an ice for 30 min, then subjected to a heat shock at 42° C. for 45 s to 90 s, and then placed on an ice for 2 min; 600 μL of an LB medium (formula: NaCl: 10 g/L, yeast powder: 5 g/L, and peptone: 10 g/L) was added, and a resulting bacterial solution was shaken on a shaker at 37° C. and 200 rpm for 45 min, then totally coated evenly on a kanamycin-resistant LB plate, and cultivated overnight at 37° C.; 2 single colonies were picked from the plate, inoculated into an LB liquid medium (formula: NaCl: 10 g/L, yeast powder: 5 g/L, and peptone: 10 g/L), and cultivated for 9 h; a resulting bacterial solution was stored in glycerin-filled tubes and subjected to sequencing, and bacteria with a correct sequencing result in a glycerin-filled tube were coated on a kanamycin-resistant LB plate (formula: NaCl: 10 g/L, yeast powder: 5 g/L, peptone: 10 g/L, and agar: 20 g/L); and a mutant recombinant plasmid was extracted from corresponding bacteria, and the mutant recombinant plasmid and a WT recombinant plasmid each were transformed into *E. coli* BL21 (DE3) to obtain a corresponding recombinant strain S195Q-McSuSy and a WT strain UGT76G1-McSuSy.

Example 4 Induced Expression for Recombinant Strains

Single colonies of each the recombinant strains G87D-StSUS1, S147D-StSUS1, SI47N-StSUS1, S195Q-StSUS1, L200Y-StSUS1, T284S-StSUS1, S285W-StSUS1, G378P-StSUS1, and S195Q-McSuSy and the WT strains UGT76G1-StSUS1 and UGT76G1-McSuSy were picked and inoculated into a shake tube with 5 mL of a liquid medium and 50 mg/L of resistance, and then the shake tube was shaken on a shaker at 37° C. and 200 rpm to allow activation for 12 h; a resulting seed solution was inoculated at an inoculum size of 3% (v:v) into a shake flask with 100 mL of an LB liquid medium and resistance, and the shake flask was shaken on a shaker at 37° C. and 200 rpm to allow activation for 2 h; and when $OD_{600}$ of a resulting bacterial solution reached 0.6 to 0.8, a temperature of the shaker was reduced to 20° C. to slow the growth of bacteria, and 0.1 mM IPTG was added to the shake flask to induce expression for 36 h.

A resulting bacterial solution was collected and subjected to frozen centrifugation at 4° C. and 7,000 rpm for 6 min, a resulting supernatant was discarded, and a resulting bacterial precipitate was rinsed twice with a potassium phosphate buffer and then suspended with an appropriate amount of a potassium phosphate buffer; a resulting bacterial suspension was placed in an ice-water mixture, subjected to ultrasonication by an ultrasonic disruptor at <D6 and 300 W for 30 min, and then centrifuged by a refrigerated centrifuge at 4° C. and 8,000 rpm for 30 min; and a resulting supernatant (namely, a crude enzyme solution) was collected and stored in a 4° C. freezer for later use.

Example 5 Preliminary Screening of Mutants Through Catalytic Reactions

Recombinases were prepared with the mutant strains G87D-StSUS1, S147D-StSUS1, S147N-StSUS1, S195Q-StSUS1, L200Y-StSUS1, T284S-StSUS1, S285W-StSUS1, and G378P-StSUS1 and the WT strain UGT76G1-StSUS1, and then used to convert RebE or RebD to preliminarily screen out relatively-preferred mutants.

The conversion of RebE adopted a 3 mL reaction system including. RebE as a substrate: 10 g/L, sucrose: 30 g/L, crude enzyme: 5 mg/mL, and 100 mM potassium phosphate buffer (pH 7.2): the balance. A RebE conversion reaction was conducted on a shaker at 40° C. and 200 rpm for 12 h, and corresponding conversion rates were shown in FIG. 1. The results showed that S147N-StSUS1 and G378P-StSUS1 exhibited basically no catalytic activity for RebE; S147D-StSUS1 had a low conversion rate for RebE; and S195Q-StSUS1, L200Y-StSUS1, T284S-StSUS1, and S285W-StSUS1 all had a substrate conversion rate of higher than 90%, which was 1.1 times a conversion rate of UGT76G1-StSUS1.

Figure 2:
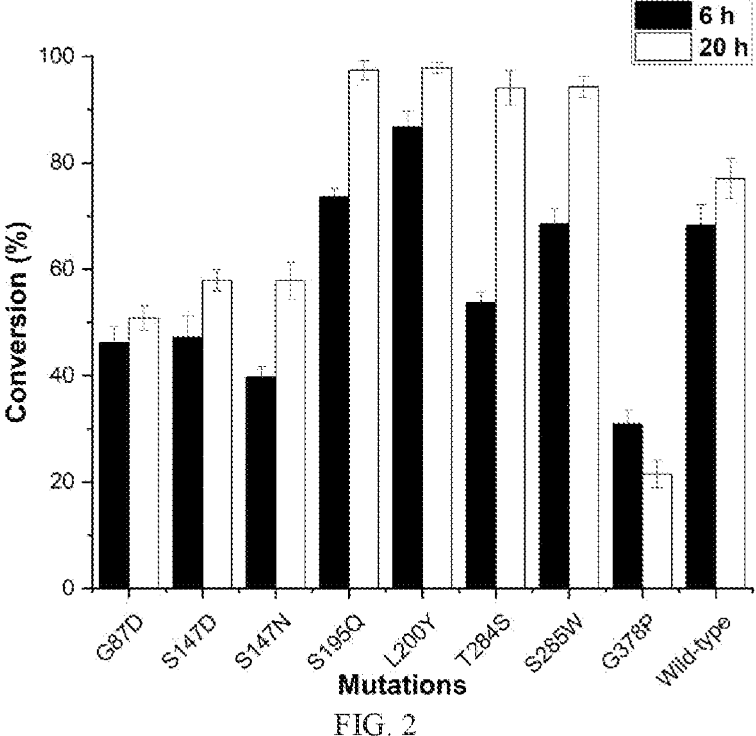
FIG. 2 shows the conversion of recombinases for RebD.

The conversion of RebD adopted a 3 mL reaction system including: RebD as a substrate: 1 g/L, sucrose: 3 g/L, crude enzyme: 5 mg/mL, and 100 mM potassium phosphate buffer (pH 7.2): the balance. A RebD conversion reaction was conducted on a shaker at 40° C. and 200 rpm for 6 h and 20 h, and corresponding conversion rates were shown in FIG. 2. The results showed that, when the RebD conversion reaction was conducted for 6 h, L200Y-StSUS1 exhibited the optimal catalytic effect, and only S195Q-StSUS1 and L200Y-StSUS1 had a substrate conversion rate of more than 70%; and when the RebD conversion reaction was conducted for 20 h, S195Q-StSUS1, L200Y-StSUS1, T284S-StSUS1, and S285W-StSUS1 all had a substrate conversion rate of higher than 95%, and S195Q-StSUS1 and L200Y-StSUS1 had equivalent substrate conversion rates, which were 1.3 times a substrate conversion rate of UGT76G1-StSUS1.

Example 6 Re-Screening of Mutants Based on Crude Enzyme Activities

Activities of glycosyltransferase mutants and a WT glycosyltransferase were determined. A 3 mL catalytic reaction system was prepared from the following components: 1.2 mM rebaudioside E, 2 mM UDPG, 3 mM $MgCl_2$, crude enzyme: 1 mg, and 100 mM potassium phosphate buffer with a pH of 7.2: the balance. A catalytic reaction was conducted on a shaker at 37° C. and 200 rpm, where a sample was collected at 0 min and 30 min. Sample treatment: 500 μL of a sample solution was pipetted and added to an EP tube; the EP tube was placed in boiling water at 95° C. for 15 min to stop a reaction, and then centrifuged in a centrifuge at 12,000 rpm for 1 min; and a resulting supernatant was collected and added to a new EP tube, filtered through an organic filter membrane (0.45 μm), and stored in a liquid-phase sample bottle for high-performance liquid chromatography (HPLC) analysis. Definition of an enzyme activity (U): an enzyme amount required for producing 1 μmol of a product within 1 min is defined as 1 enzyme activity unit.

Figures 3, 4:
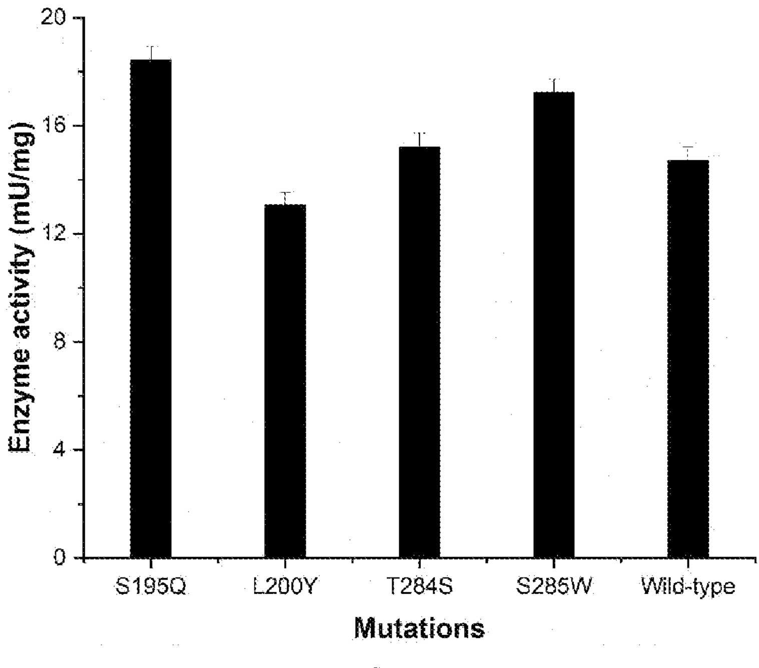
FIG. 3 shows the enzyme activities of mutants and WT UGT76G1.
FIG. 4 shows an impact of coupling of different SuSy with different glycosyltransferases on synthesis of a Reb M product.

The four mutant strains S195Q-StSUS1, L200Y-StSUS1, T284S-StSUS1, and S285W-StSUS1 screened out in the above conversion experiment were used to produce glycosyltransferase mutants, and the glycosyltransferase mutants and the WT glycosyltransferase UGT76G1 were tested for activities. As shown in FIG. 3, L200Y exhibited a low enzyme activity, which was lower than an enzyme activity of the WT glycosyltransferase UGT76G1; and S195Q exhibited the highest enzyme activity, which was 1.3 times an enzyme activity of the WT glycosyltransferase UGT76G1. Thus, the optimal mutant strain S195Q-StSUS1 was screened out.

Example 7 Impact of Coupling of Different SuSy with Different Glycosyltransferases on Synthesis of a Reb M Product A 3 mL catalytic reaction system was prepared from the following components: rebaudioside D as a substrate: 1 g/L, sucrose: 5 g/L, crude enzyme: 5 mg/mL, and 100 mM potassium phosphate buffer (pH 7.2): the balance. A catalytic reaction was conducted on a shaker at 30° C. and 200 rpm for 6 h, where 500 μL of a sample solution was collected in an EP tube at a specified time interval, then placed in boiling water at 95° C. for 15 min to stop a reaction, and then centrifuged in a centrifuge at 12,000 rpm for 1 min; and a resulting supernatant was transferred to a new EP tube, diluted to a concentration of lower than 1 g/L, and then subjected to HPLC analysis. As shown in FIG. 4, after the catalytic reaction was conducted for 6 h, a yield of 1.27 g/L RebM converted by S195Q-McSuSy was 1.6, 2.6, and 2.7 times of a yield of 1.27 g/L RebM converted by UGT76G1-McSuSy, a yield of 1.27 g/L RebM converted by S195Q-StSUS1, and a yield of 1.27 g/L RebM converted by UGT76G1-StSUS1, respectively; and a yield of RebM converted by UGT76G1-McSuSy was 1.8 times a yield of RebM converted by UGT76G1-StSUS1. Therefore, McSuSy is more suitable than StSUS1 for co-expression with UGT76G1 and S195Q to improve the synthesis of RebM.

Figure 5:
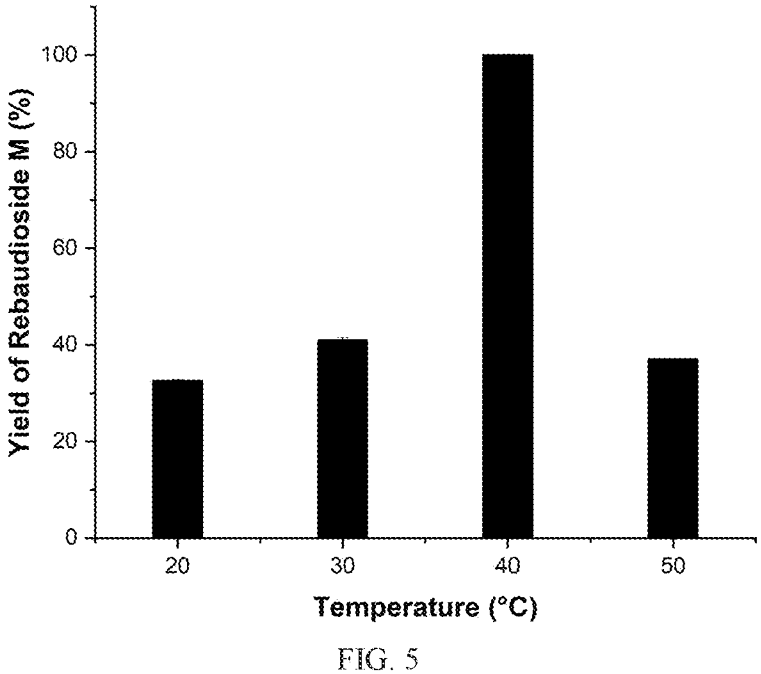
FIG. 5 shows an impact of different reaction temperatures on synthesis of a Reb M product.

Example 8 Impact of Different Reaction Temperatures on Synthesis of a Reb M Product A 3 mL catalytic reaction system was prepared from the following components: rebaudioside E: 20 g/L, sucrose: 100 g/L, crude enzyme: 3 mg/mL, and 100 mM potassium phosphate buffer (pH 7.2): the balance. A catalytic reaction was conducted on a shaker at 20° C. to 50° C. and 200 rpm for 22 h, where 500 μL of a sample solution was collected in an EP tube at a specified time interval, then placed in boiling water at 95° C. for 15 min to stop a reaction, and then centrifuged in a centrifuge at 12,000 rpm for 1 min; and a resulting supernatant was transferred to a new EP tube, diluted to a concentration of lower than 1 g/L, and then subjected to HPLC analysis. As shown in FIG. 5, when a reaction temperature was 40° C., the recombinase S195Q-McSuSy led to the highest RebM yield of 8.162 g/L, which was 1.3 times higher than a RebM yield of the original enzyme UGT76G1-McSuSy. Thus, the optimal temperature was 40° C.

Figure 6:
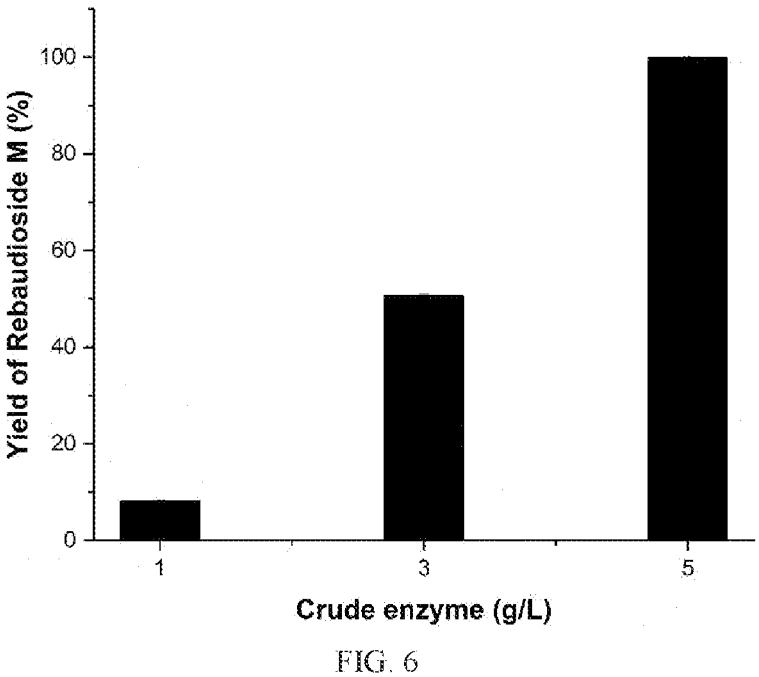
FIG. 6 shows an impact of different crude enzyme concentrations on synthesis of a Reb M product.

Example 9 Impact of Different Crude Enzyme Concentrations on Synthesis of a Reb M Product A 3 mL catalytic reaction system was prepared from the following components: rebaudioside E: 20 g/L, sucrose: 100 g/L, crude enzyme: 1 mg/mL to 5 mg/mL, and 100 mM potassium phosphate buffer (pH 7.2): the balance. A catalytic reaction was conducted on a shaker at 40° C. and 200 rpm for 22 h, where 500 μL of a sample solution was collected in an EP tube at a specified time interval, then placed in boiling water at 95° C. for 15 min to stop a reaction, and then centrifuged in a centrifuge at 12,000 rpm for 1 min; and a resulting supernatant was transferred to a new EP tube, diluted to a concentration of lower than 1 g/L, and then subjected to HPLC analysis. As shown in FIG. 6, when a concentration of the crude recombinase S195Q-McSuSy was 5 mg/mL, the highest RebM yield of 9.756 g/L was allowed, which was 1.5 times higher than a RebM yield of the original enzyme UGT76G1-McSuSy under the same reaction conditions. Therefore, the optimal crude recombinase S195Q-McSuSy concentration was 5 mg/mL.

Figure 7:
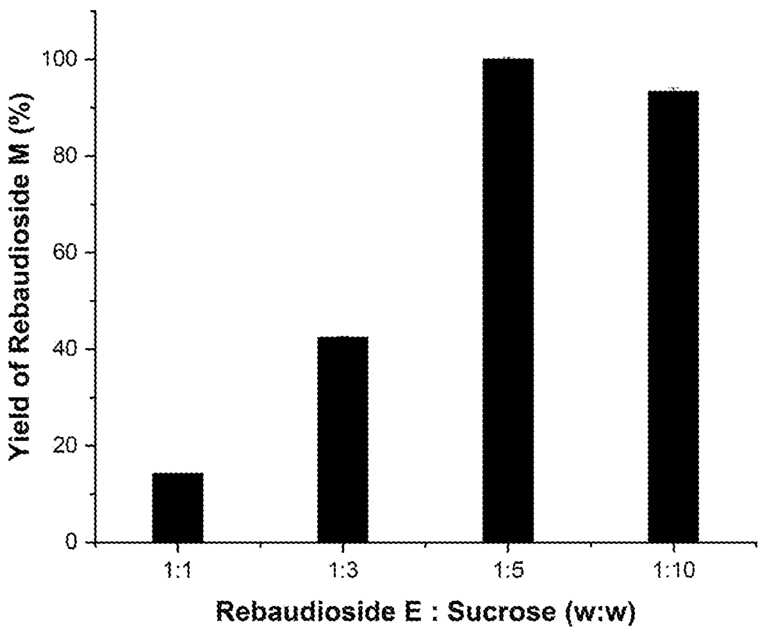
FIG. 7 shows an impact of different concentration ratios of Reb E to sucrose on synthesis of a Reb M product.

Example 10 Impact of Different Concentration Ratios of Reb E to Sucrose on Synthesis of a Reb M Product A 3 mL catalytic reaction system was prepared from the following components: rebaudioside E: 20 g/L, sucrose: 20 g/L to 200 g/L, crude enzyme: 5 mg/mL, and 100 mM potassium phosphate buffer (pH 7.2): the balance. A catalytic reaction was conducted on a shaker at 40° C. and 200 rpm for 22 h, where 500 μL of a sample solution was collected in an EP tube at a specified time interval, then placed in boiling water at 95° C. for 15 min to stop a reaction, and then centrifuged in a centrifuge at 12,000 rpm for 1 min; and a resulting supernatant was transferred to a new EP tube, diluted to a concentration of lower than 1 g/L, and then subjected to HPLC analysis. As shown in FIG. 7, when a concentration ratio of Reb E to sucrose was 1:5, the recombinase S195Q-McSuSy led to the highest RebM yield of 10.270 g/L, which was 1.6 times higher than a RebM yield of the original enzyme UGT76G1-McSuSy under the same reaction conditions. Therefore, the optimal concentration ratio of Reb E to sucrose was 1:5, that is, a concentration of Reb E was 20 g/L and a concentration of sucrose was 100 g/L.

Figure 8:
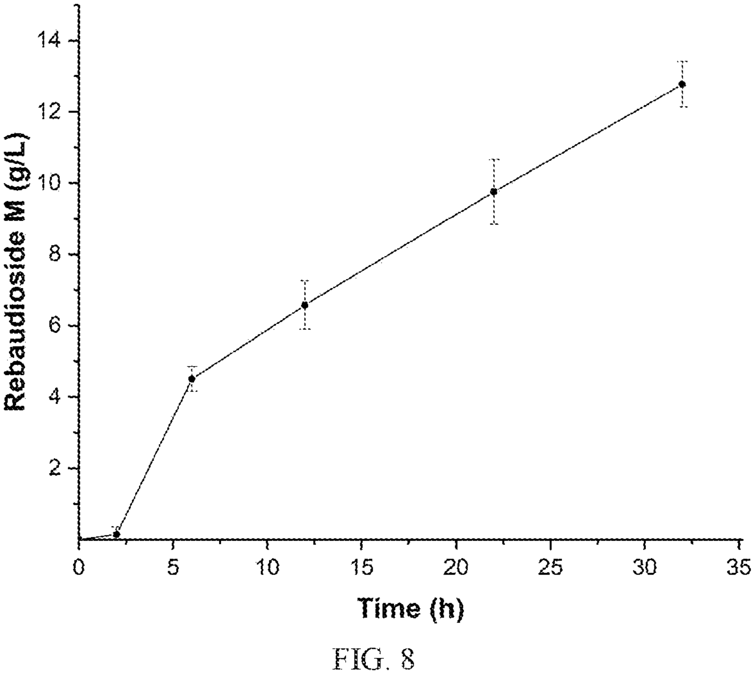
FIG. 8 shows the synthesis of a Reb M product under optimal conditions.

Example 11 Synthesis of a Reb M Product from Rebaudioside E Under Optimal Conditions A 3 mL catalytic reaction system was prepared from the following components: rebaudioside E: 20 g/L, sucrose: 100 g/L, crude enzyme: 5 mg/mL, and 100 mM potassium phosphate buffer (pH 7.2): the balance. A catalytic reaction was conducted on a shaker at 40° C. and 200 rpm for 0 h to 32 h, where 500 μL of a sample solution was collected in an EP tube at a specified time interval, then placed in boiling water at 95° C. for 15 min to stop a reaction, and then centrifuged in a centrifuge at 12,000 rpm for 1 min; and a resulting supernatant was transferred to a new EP tube, diluted to a concentration of lower than 1 g/L, and then subjected to HPLC analysis. As shown in FIG. 8, when the catalytic reaction was conducted for 0 h to 32 h, RebM was continuously synthesized and accumulated under catalysis of the recombinase S195Q-McSuSy, indicating that the recombinase could allow the continuous accumulation of RebM within a long period of time, which has a promising application prospect. When the catalytic reaction was conducted for 32 h, a concentration of RebM synthesized by the recombinase S195Q-McSuSy was 12.8 g/L, which was twice a concentration of RebM synthesized by the WT UGT76G1-McSuSy.

Example 12 Determination of Kinetic Parameters of Glycosyltransferases

A final concentration of rebaudioside E was set to 10 μM to 2,000 μM or a final concentration of rebaudioside D was set to 50 μM to 2,000 μM. Rebaudioside E or rebaudioside D solutions of different concentrations each were mixed with an appropriate amount of each of the purified WT UGT76G1 and the mutant S195Q, and an enzyme activity was determined according to the enzyme activity assay method described above. A Michaelis Menten equation was used to calculate Kn, $V_{max}$, $K_{eat}$, and $K_{eat}/K_m$ of the purified WT glycosyltransferase and the glycosyltransferase mutant. As shown in Table 1, $K_m$ values of the mutant S195Q for rebaudioside E and rebaudioside D were 56.34±2.02 μM and 214.48±14.54 μM, respectively, and $K_{eat}/K_m$ values of the mutant S195Q for rebaudioside E and rebaudioside D were 26.27 $s^{-1}$ $mM^{-1}$ and 1.17 $s^{-1}$ $mM^{-1}$, respectively; and compared with the WT UGT76G1 (corresponding $K_m$ values were 170.13±12.61 sM and 478.12i33.03 μM, respectively, and corresponding $K_{eat}/K_m$ values were 11.76 $s^{-1}$ $mM^{-1}$ and 0.42 $s^{-1}$ $mM^{-1}$, respectively), affinities of the glycosyltransferase mutant produced by the present disclosure for the substrates rebaudioside E and rebaudioside D increased by about 3.0 times and 2.2 times, respectively, and catalytic efficiencies of the glycosyltransferase mutant for the substrates rebaudioside E and rebaudioside D increased by 2.2 times and 2.8 times, respectively, which will lay an excellent foundation for industrialization of the glycosyltransferase and application of the glycosyltransferase in the food industry.

TABLE 1

Kinetic parameters of the WT UGT76G1 and the mutant S195Q

| | $K_m$ (μM) | $K_{cat}$ ($s^{-1}$) | $K_{cat}/K_m$ ($s^{-1}$ $mM^{-1}$) |
|---|---|---|---|
| UGT76G1 | | | |
| RebE | 170.13 ± 12.61 | 2.00 ± 0.03 | 11.76 |
| RebD | 478.12 ± 33.03 | 0.20 ± 0.005 | 0.42 |
| S195Q | | | |
| RebE | 56.34 ± 2.02 | 1.48 ± 0.01 | 26.27 |
| RebD | 214.48 ± 14.54 | 0.25 ± 0.004 | 1.17 |

What is claimed is:

1. A method for synthesizing rebaudioside M using a glycosyltransferase mutant, wherein the glycosyltransferase mutant is a G87D, S147D, S195Q, L200Y, S285W, or G378P mutant of the glycosyltransferase of SEQ ID NO: 1, the method comprising the following steps:

1) cloning a coding gene for said glycosyltransferase UGT76G1 mutant and a coding gene for sucrose synthase (SuSy) into an expression vector to obtain a recombinant plasmid;

2) transforming the recombinant plasmid into *Escherichia coli* (*E. coli*) BL21 (DE3) to obtain a recombinant strain, wherein the glycosyltransferase mutant and the SuSy are co-expressed in the recombinant strain;

3) inoculating the recombinant strain into an Luria-Bertani (LB) liquid medium, and adding an inducer into the LB liquid medium to induce an expression; centrifuging a resulting bacterial solution at 4° C., collecting a resulting bacterial precipitate, and resuspending the bacterial precipitate with a predetermined buffer; and subjecting a resulting bacterial suspension to an ultrasonication, centrifuging a resulting ultrasonication system, and collecting a first resulting supernatant, wherein the first resulting supernatant is a crude enzyme solution; and 4) adding rebaudioside E or rebaudioside D as a substrate, sucrose, and the crude enzyme solution to a catalytic reaction system, and allowing a reaction at a predetermined temperature; and collecting a sample, inactivating the sample at 95° C., centrifuging an inactivated sample, and collecting a second resulting supernatant, wherein the second resulting supernatant is the rebaudioside M.

2. The method according to claim 1, wherein the inducer is isopropyl-β-D-thiogalactoside, the inducer is added at a concentration of 0.1 mM to 1.0 mM, and the expression is induced for 20 h to 40 h.

3. The method according to claim 1, wherein in the catalytic reaction system, a concentration of the rebaudioside E is 10 g/L to 50 g/L, a concentration of the sucrose is 10 g/L to 200 g/L, and a concentration of the crude enzyme solution is 1 g/L to 5 g/L, and the reaction is conducted at 20° C. to 50° C. for 2 h to 32 h.

4. The method according to claim 1, wherein in the catalytic reaction system, a concentration of the rebaudioside D is 1 g/L to 5 g/L, a concentration of the sucrose is 1 g/L to 20 g/L, and a concentration of the crude enzyme solution is 1 g/L to 5 g/L; and the reaction is conducted at 20° C. to 50° C. for 2 h to 32 h.

5. The method according to claim 1, wherein the SuSy is StSUS1 or McSuSy, the nucleotide sequence for the StSUS1 is shown in SEQ ID NO: 11 and the nucleotide sequence for the McSuSy is shown in SEQ ID NO: 12.

6. The method according to claim 1, wherein the nucleotide sequence for the glycosyltransferase mutant G87D is shown in SEQ ID NO: 3, the nucleotide sequence for the glycosyltransferase mutant S147D is shown in SEQ ID NO: 4 the nucleotide sequence for the glycosyltransferase mutant S195Q is shown in SEQ ID NO: 6, the nucleotide sequence for the glycosyltransferase mutant L200Y is shown in SEQ ID NO: 7, the nucleotide sequence for the glycosyltransferase mutant S285S is shown in SEQ ID NO: 9, and the nucleotide sequence for the glycosyltransferase mutant G378P is shown in SEQ ID NO: 10.

* * * * *

SEQUENCE LISTING

```
Sequence total quantity: 28
SEQ ID NO: 1            moltype = AA  length = 458
FEATURE                 Location/Qualifiers
REGION                  1..458
                        note = The sequence is synthetized.
source                  1..458
                        mol_type = protein
                        organism = synthetic construct
SEQUENCE: 1
MENKTETTVR RRRRIILFPV PFQGHINPIL QLANVLYSKG FSITIFHTNF NKPKTSNYPH  60
FTFRFILDND PQDERISNLP THGPLAGMRI PIINEHGADE LRRELELLML ASEEDEEVSC  120
LITDALWYFA QSVADSLNLR RLVLMTSSLF NFHAHVSLPQ FDELGYLDPD DKTRLEEQAS  180
GFPMLKVKDI KSAYSNWQIL KEILGKMIKQ TKASSGVIWN SFKELEESEL ETVIREIPAP  240
SFLIPLPKHL TASSSSLLDH DRTVFQWLDQ QPPSSVLYVS FGSTSEVDEK DFLEIARGLV  300
DSKQSFLWVV RPGFVKGSTW VEPLPDGFLG ERGRIVKWVP QQEVLAHGAI GAFWTHSGWN  360
STLESVCEGV PMIFSDFGLD QPLNARYMSD VLKVGVYLEN GWERGEIANA IRRVMVDEEG  420
EYIRQNARVL KQKADVSLMK GGSSYESLES LVSYISSL                        458

SEQ ID NO: 2            moltype = DNA  length = 1377
FEATURE                 Location/Qualifiers
misc_feature            1..1377
                        note = The sequence is synthetized.
source                  1..1377
                        mol_type = other DNA
                        organism = synthetic construct
SEQUENCE: 2
atggaaaata aaaccgaaac caccgtccgc cgtcgtcgcc gtatcattct gttcccggtc  60
ccgttccagg gccacatcaa cccgattctg caactggcga acgtgctgta ttcgaaaggt  120
ttcagcatca ccatcttcca tacgaacttc aacaagccga agaccagcaa ttacccgcac  180
tttacgttcc gttttattct ggataacgac ccgcaggatg aacgcatctc taatctgccg  240
acccacggcc cgctggcggg tatgcgtatt ccgattatca acgaacacgg cgcagatgaa  300
ctgcgtcgcg aactggaact gctgatgctg gccagcgaag aagatgaaga agtttcttgc  360
ctgatcaccg acgcactgtg gtattttgcc cagtctgttg cagatagtct gaacctgcgt  420
cgcctggtcc tgatgaccag cagcctgttc aattttcatg cccacgttag tctgccgcag  480
ttcgatgaac tgggttatct ggacccggat gacaaaaccc gcctggaaga acaggcgagc  540
```

```
ggctttccga tgctgaaagt caaggatatt aagtcagcgt actcgaactg gcagattctg  600
aaagaaatcc tgggtaaaat gattaagcaa accaaagcaa gttccggcgt catctggaat  660
agtttcaaag aactggaaga atccgaactg gaaacggtga ttcgtgaaat cccggctccg  720
agttttctga ttccgctgcc gaagcatctg accgcgagca gcagcagcct gctggatcac  780
gaccgcacgg tgtttcagtg gctggatcag caaccgccga gttccgtgct gtatgttagc  840
ttcggtagta cctcggaagt ggatgaaaag gactttctgg aaatcgctcg tggcctggtt  900
gatagcaaac aatctttcct gtgggtggtt cgcccgggtt ttgtgaaggg ctctacgtgg  960
gttgaaccgc tgccggacgg cttcctgggt gaacgtggcc gcattgtcaa atgggtgccg  1020
cagcaagaag tgctggcgca tggcgcgatt ggcgcgtttt ggacccactc cggttggaac  1080
tcaacgctgg aatcggtttg tgaaggtgtc ccgatgattt tctcagattt tggcctggac  1140
cagccgctga atgcacgtta tatgtcggat gttctgaaag tcggtgtgta cctggaaaac  1200
ggttgggaac gcggcgaaat tgcgaatgcc atccgtcgcg ttatggtcga tgaagaaggc  1260
gaatacattc gtcagaatgc tcgcgtcctg aaacaaaagg cggacgtgag cctgatgaaa  1320
ggcggttcat cgtatgaaag tctggaatcc ctggtttcat acatcagctc tctgtaa     1377

SEQ ID NO: 3            moltype = DNA  length = 1377
FEATURE                 Location/Qualifiers
misc_feature            1..1377
                        note = The sequence is synthetized.
source                  1..1377
                        mol_type = other DNA
                        organism = synthetic construct
SEQUENCE: 3
atggaaaata aaaccgaaac caccgtccgc cgtcgtcgcc gtatcattct gttcccggtc  60
ccgttccagg gccacatcaa cccgattctg caactggcga acgtgctgta ttcgaaaggt  120
ttcagcatca ccatcttcca tacgaacttc aacaagccga agaccagcaa ttacccgcac  180
tttacgttcc gttttattct ggataacgac ccgcaggatg aacgcatctc taatctgccg  240
acccacggcc cgctggcgga catgcgtatt ccgattatca acgaacacgg cgcagatgaa  300
ctgcgtcgcg aactggaact gctgatgctg gccagcgaag aagatgaaga agtttcttgc  360
ctgatcaccg acgcactgtg gtattttgcc cagtctgttg cagatagtct gaacctgcgt  420
cgcctggtcc tgatgaccag cagcctgttc aattttcatg cccacgttag tctgccgcag  480
ttcgatgaac tgggttatct ggacccggat gacaaaaccc gcctggaaga acaggcgagc  540
ggctttccga tgctgaaagt caaggatatt aagtcagcgt actcgaactg gcagattctg  600
aaagaaatcc tgggtaaaat gattaagcaa accaaagcaa gttccggcgt catctggaat  660
agtttcaaag aactggaaga atccgaactg gaaacggtga ttcgtgaaat cccggctccg  720
agttttctga ttccgctgcc gaagcatctg accgcgagca gcagcagcct gctggatcac  780
gaccgcacgg tgtttcagtg gctggatcag caaccgccga gttccgtgct gtatgttagc  840
ttcggtagta cctcggaagt ggatgaaaag gactttctgg aaatcgctcg tggcctggtt  900
gatagcaaac aatctttcct gtgggtggtt cgcccgggtt ttgtgaaggg ctctacgtgg  960
gttgaaccgc tgccggacgg cttcctgggt gaacgtggcc gcattgtcaa atgggtgccg  1020
cagcaagaag tgctggcgca tggcgcgatt ggcgcgtttt ggacccactc cggttggaac  1080
tcaacgctgg aatcggtttg tgaaggtgtc ccgatgattt tctcagattt tggcctggac  1140
cagccgctga atgcacgtta tatgtcggat gttctgaaag tcggtgtgta cctggaaaac  1200
ggttgggaac gcggcgaaat tgcgaatgcc atccgtcgcg ttatggtcga tgaagaaggc  1260
gaatacattc gtcagaatgc tcgcgtcctg aaacaaaagg cggacgtgag cctgatgaaa  1320
ggcggttcat cgtatgaaag tctggaatcc ctggtttcat acatcagctc tctgtaa     1377

SEQ ID NO: 4            moltype = DNA  length = 1377
FEATURE                 Location/Qualifiers
misc_feature            1..1377
                        note = The sequence is synthetized.
source                  1..1377
                        mol_type = other DNA
                        organism = synthetic construct
SEQUENCE: 4
atggaaaata aaaccgaaac caccgtccgc cgtcgtcgcc gtatcattct gttcccggtc  60
ccgttccagg gccacatcaa cccgattctg caactggcga acgtgctgta ttcgaaaggt  120
ttcagcatca ccatcttcca tacgaacttc aacaagccga agaccagcaa ttacccgcac  180
tttacgttcc gttttattct ggataacgac ccgcaggatg aacgcatctc taatctgccg  240
acccacggcc cgctggcggg tatgcgtatt ccgattatca acgaacacgg cgcagatgaa  300
ctgcgtcgcg aactggaact gctgatgctg gccagcgaag aagatgaaga agtttcttgc  360
ctgatcaccg acgcactgtg gtattttgcc cagtctgttg cagatagtct gaacctgcgt  420
cgcctggtcc tgatgaccga cagcctgttc aattttcatg cccacgttag tctgccgcag  480
ttcgatgaac tgggttatct ggacccggat gacaaaaccc gcctggaaga acaggcgagc  540
ggctttccga tgctgaaagt caaggatatt aagtcagcgt actcgaactg gcagattctg  600
aaagaaatcc tgggtaaaat gattaagcaa accaaagcaa gttccggcgt catctggaat  660
agtttcaaag aactggaaga atccgaactg gaaacggtga ttcgtgaaat cccggctccg  720
agttttctga ttccgctgcc gaagcatctg accgcgagca gcagcagcct gctggatcac  780
gaccgcacgg tgtttcagtg gctggatcag caaccgccga gttccgtgct gtatgttagc  840
ttcggtagta cctcggaagt ggatgaaaag gactttctgg aaatcgctcg tggcctggtt  900
gatagcaaac aatctttcct gtgggtggtt cgcccgggtt ttgtgaaggg ctctacgtgg  960
gttgaaccgc tgccggacgg cttcctgggt gaacgtggcc gcattgtcaa atgggtgccg  1020
cagcaagaag tgctggcgca tggcgcgatt ggcgcgtttt ggacccactc cggttggaac  1080
tcaacgctgg aatcggtttg tgaaggtgtc ccgatgattt tctcagattt tggcctggac  1140
cagccgctga atgcacgtta tatgtcggat gttctgaaag tcggtgtgta cctggaaaac  1200
ggttgggaac gcggcgaaat tgcgaatgcc atccgtcgcg ttatggtcga tgaagaaggc  1260
gaatacattc gtcagaatgc tcgcgtcctg aaacaaaagg cggacgtgag cctgatgaaa  1320
ggcggttcat cgtatgaaag tctggaatcc ctggtttcat acatcagctc tctgtaa     1377
```

-continued

```
SEQ ID NO: 5            moltype = DNA  length = 1377
FEATURE                 Location/Qualifiers
misc_feature            1..1377
                        note = The sequence is synthetized.
source                  1..1377
                        mol_type = other DNA
                        organism = synthetic construct
SEQUENCE: 5
atggaaaata aaaccgaaac caccgtccgc cgtcgtcgcc gtatcattct gttcccggtc  60
ccgttccagg gccacatcaa cccgattctg caactggcga acgtgctgta ttcgaaaggt  120
ttcagcatca ccatcttcca tacgaacttc aacaagccga agaccagcaa ttacccgcac  180
tttacgttcc gttttattct ggataacgac ccgcaggatg aacgcatctc taatctgccg  240
acccacggcc cgctggcggg tatgcgtatt ccgattatca acgaacacgg cgcagatgaa  300
ctgcgtcgcg aactggaact gctgatgctg gccagcgaag aagatgaaga agtttcttgc  360
ctgatcaccg acgcactgtg gtattttgcc cagtctgttg cagatagtct gaacctgcgt  420
cgcctggtcc tgatgaccaa cagcctgttc aattttcatg cccacgttag tctgccgcag  480
ttcgatgaac tgggttatct ggacccggat gacaaaaccc gcctggaaga acaggcgagc  540
ggctttccga tgctgaaagt caaggatatt aagtcagcgt actcgaactg gcagattctg  600
aaagaaatcc tgggtaaaat gattaagcaa accaaagcaa gttccggcgt catctggaat  660
agtttcaaag aactggaaga atccgaactg gaaacggtga ttcgtgaaat cccggctccg  720
agttttctga ttccgctgcc gaagcatctg accgcgagca gcagcagcct gctggatcac  780
gaccgcacgg tgtttcagtg gctggatcag caaccgccga gttccgtgct gtatgttagc  840
ttcggtagta cctcggaagt ggatgaaaag gactttctgg aaatcgctcg tggcctggtt  900
gatagcaaac aatctttcct gtgggtggtt cgcccgggtt ttgtgaaggg ctctacgtgg  960
gttgaaccgc tgccggacgg cttcctgggt gaacgtggcc gcattgtcaa atgggtgccg  1020
cagcaagaag tgctggcgca tggcgcgatt ggcgcgtttt ggacccactc cggttggaac  1080
tcaacgctgg aatcggtttg tgaaggtgtc ccgatgattt tctcagattt tggcctggac  1140
cagccgctga atgcacgtta tatgtcggat gttctgaaag tcggtgtgta cctggaaaac  1200
ggttgggaac gcggcgaaat tgcgaatgcc atccgtcgcg ttatggtcga tgaagaaggc  1260
gaatacattc gtcagaatgc tcgcgtcctg aaacaaaagg cggacgtgag cctgatgaaa  1320
ggcggttcat cgtatgaaag tctggaatcc ctggtttcat acatcagctc tctgtaa     1377

SEQ ID NO: 6            moltype = DNA  length = 1377
FEATURE                 Location/Qualifiers
misc_feature            1..1377
                        note = The sequence is synthetized.
source                  1..1377
                        mol_type = other DNA
                        organism = synthetic construct
SEQUENCE: 6
atggaaaata aaaccgaaac caccgtccgc cgtcgtcgcc gtatcattct gttcccggtc  60
ccgttccagg gccacatcaa cccgattctg caactggcga acgtgctgta ttcgaaaggt  120
ttcagcatca ccatcttcca tacgaacttc aacaagccga agaccagcaa ttacccgcac  180
tttacgttcc gttttattct ggataacgac ccgcaggatg aacgcatctc taatctgccg  240
acccacggcc cgctggcggg tatgcgtatt ccgattatca acgaacacgg cgcagatgaa  300
ctgcgtcgcg aactggaact gctgatgctg gccagcgaag aagatgaaga agtttcttgc  360
ctgatcaccg acgcactgtg gtattttgcc cagtctgttg cagatagtct gaacctgcgt  420
cgcctggtcc tgatgaccag cagcctgttc aattttcatg cccacgttag tctgccgcag  480
ttcgatgaac tgggttatct ggacccggat gacaaaaccc gcctggaaga acaggcgagc  540
ggctttccga tgctgaaagt caaggatatt aagtcagcgt accaaaactg gcagattctg  600
aaagaaatcc tgggtaaaat gattaagcaa accaaagcaa gttccggcgt catctggaat  660
agtttcaaag aactggaaga atccgaactg gaaacggtga ttcgtgaaat cccggctccg  720
agttttctga ttccgctgcc gaagcatctg accgcgagca gcagcagcct gctggatcac  780
gaccgcacgg tgtttcagtg gctggatcag caaccgccga gttccgtgct gtatgttagc  840
ttcggtagta cctcggaagt ggatgaaaag gactttctgg aaatcgctcg tggcctggtt  900
gatagcaaac aatctttcct gtgggtggtt cgcccgggtt ttgtgaaggg ctctacgtgg  960
gttgaaccgc tgccggacgg cttcctgggt gaacgtggcc gcattgtcaa atgggtgccg  1020
cagcaagaag tgctggcgca tggcgcgatt ggcgcgtttt ggacccactc cggttggaac  1080
tcaacgctgg aatcggtttg tgaaggtgtc ccgatgattt tctcagattt tggcctggac  1140
cagccgctga atgcacgtta tatgtcggat gttctgaaag tcggtgtgta cctggaaaac  1200
ggttgggaac gcggcgaaat tgcgaatgcc atccgtcgcg ttatggtcga tgaagaaggc  1260
gaatacattc gtcagaatgc tcgcgtcctg aaacaaaagg cggacgtgag cctgatgaaa  1320
ggcggttcat cgtatgaaag tctggaatcc ctggtttcat acatcagctc tctgtaa     1377

SEQ ID NO: 7            moltype = DNA  length = 1377
FEATURE                 Location/Qualifiers
misc_feature            1..1377
                        note = The sequence is synthetized.
source                  1..1377
                        mol_type = other DNA
                        organism = synthetic construct
SEQUENCE: 7
atggaaaata aaaccgaaac caccgtccgc cgtcgtcgcc gtatcattct gttcccggtc  60
ccgttccagg gccacatcaa cccgattctg caactggcga acgtgctgta ttcgaaaggt  120
ttcagcatca ccatcttcca tacgaacttc aacaagccga agaccagcaa ttacccgcac  180
tttacgttcc gttttattct ggataacgac ccgcaggatg aacgcatctc taatctgccg  240
acccacggcc cgctggcggg tatgcgtatt ccgattatca acgaacacgg cgcagatgaa  300
ctgcgtcgcg aactggaact gctgatgctg gccagcgaag aagatgaaga agtttcttgc  360
ctgatcaccg acgcactgtg gtattttgcc cagtctgttg cagatagtct gaacctgcgt  420
```

```
cgcctggtcc tgatgaccag cagcctgttc aattttcatg cccacgttag tctgccgcag  480
ttcgatgaac tgggttatct ggacccggat gacaaaaccc gcctggaaga acaggcgagc  540
ggctttccga tgctgaaagt caaggatatt aagtcagcgt actcgaactg gcagatttac  600
aaagaaatcc tgggtaaaat gattaagcaa accaaagcaa gttccggcgt catctggaat  660
agtttcaaag aactggaaga atccgaactg gaaacggtga ttcgtgaaat cccggctccg  720
agttttctga ttccgctgcc gaagcatctg accgcgagca gcagcagcct gctggatcac  780
gaccgcacgg tgtttcagtg gctggatcag caaccgccga gttccgtgct gtatgttagc  840
ttcggtagta cctcggaagt ggatgaaaag gactttctgg aaatcgctcg tggcctggtt  900
gatagcaaac aatctttcct gtgggtggtt cgcccgggtt ttgtgaaggg ctctacgtgg  960
gttgaaccgc tgccggacgg cttcctgggt gaacgtggcc gcattgtcaa atgggtgccg  1020
cagcaagaag tgctggcgca tggcgcgatt ggcgcgtttt ggacccactc cggttggaac  1080
tcaacgctgg aatcggtttg tgaaggtgtc ccgatgattt tctcagattt tggcctggac  1140
cagccgctga atgcacgtta tatgtcggat gttctgaaag tcggtgtgta cctggaaaac  1200
ggttgggaac gcggcgaaat tgcgaatgcc atccgtcgcg ttatggtcga tgaagaaggc  1260
gaatacattc gtcagaatgc tcgcgtcctg aaacaaaagg cggacgtgag cctgatgaaa  1320
ggcggttcat cgtatgaaag tctggaatcc ctggtttcat acatcagctc tctgtaa     1377

SEQ ID NO: 8           moltype = DNA  length = 1377
FEATURE                Location/Qualifiers
misc_feature           1..1377
                       note = The sequence is synthetized.
source                 1..1377
                       mol_type = other DNA
                       organism = synthetic construct
SEQUENCE: 8
atggaaaata aaaccgaaac caccgtccgc cgtcgtcgcc gtatcattct gttcccggtc  60
ccgttccagg gccacatcaa cccgattctg caactggcga acgtgctgta ttcgaaaggt  120
ttcagcatca ccatcttcca tacgaacttc aacaagccga agaccagcaa ttacccgcac  180
tttacgttcc gttttattct ggataacgac ccgcaggatg aacgcatctc taatctgccg  240
acccacggcc cgctggcggg tatgcgtatt ccgattatca acgaacacgg cgcagatgaa  300
ctgcgtcgcg aactggaact gctgatgctg gccagcgaag aagatgaaga agtttcttgc  360
ctgatcaccg acgcactgtg gtattttgcc cagtctgttg cagatagtct gaacctgcgt  420
cgcctggtcc tgatgaccag cagcctgttc aattttcatg cccacgttag tctgccgcag  480
ttcgatgaac tgggttatct ggacccggat gacaaaaccc gcctggaaga acaggcgagc  540
ggctttccga tgctgaaagt caaggatatt aagtcagcgt actcgaactg gcagattctg  600
aaagaaatcc tgggtaaaat gattaagcaa accaaagcaa gttccggcgt catctggaat  660
agtttcaaag aactggaaga atccgaactg gaaacggtga ttcgtgaaat cccggctccg  720
agttttctga ttccgctgcc gaagcatctg accgcgagca gcagcagcct gctggatcac  780
gaccgcacgg tgtttcagtg gctggatcag caaccgccga gttccgtgct gtatgttagc  840
ttcggtagta gctcggaagt ggatgaaaag gactttctgg aaatcgctcg tggcctggtt  900
gatagcaaac aatctttcct gtgggtggtt cgcccgggtt ttgtgaaggg ctctacgtgg  960
gttgaaccgc tgccggacgg cttcctgggt gaacgtggcc gcattgtcaa atgggtgccg  1020
cagcaagaag tgctggcgca tggcgcgatt ggcgcgtttt ggacccactc cggttggaac  1080
tcaacgctgg aatcggtttg tgaaggtgtc ccgatgattt tctcagattt tggcctggac  1140
cagccgctga atgcacgtta tatgtcggat gttctgaaag tcggtgtgta cctggaaaac  1200
ggttgggaac gcggcgaaat tgcgaatgcc atccgtcgcg ttatggtcga tgaagaaggc  1260
gaatacattc gtcagaatgc tcgcgtcctg aaacaaaagg cggacgtgag cctgatgaaa  1320
ggcggttcat cgtatgaaag tctggaatcc ctggtttcat acatcagctc tctgtaa     1377

SEQ ID NO: 9           moltype = DNA  length = 1377
FEATURE                Location/Qualifiers
misc_feature           1..1377
                       note = The sequence is synthetized.
source                 1..1377
                       mol_type = other DNA
                       organism = synthetic construct
SEQUENCE: 9
atggaaaata aaaccgaaac caccgtccgc cgtcgtcgcc gtatcattct gttcccggtc  60
ccgttccagg gccacatcaa cccgattctg caactggcga acgtgctgta ttcgaaaggt  120
ttcagcatca ccatcttcca tacgaacttc aacaagccga agaccagcaa ttacccgcac  180
tttacgttcc gttttattct ggataacgac ccgcaggatg aacgcatctc taatctgccg  240
acccacggcc cgctggcggg tatgcgtatt ccgattatca acgaacacgg cgcagatgaa  300
ctgcgtcgcg aactggaact gctgatgctg gccagcgaag aagatgaaga agtttcttgc  360
ctgatcaccg acgcactgtg gtattttgcc cagtctgttg cagatagtct gaacctgcgt  420
cgcctggtcc tgatgaccag cagcctgttc aattttcatg cccacgttag tctgccgcag  480
ttcgatgaac tgggttatct ggacccggat gacaaaaccc gcctggaaga acaggcgagc  540
ggctttccga tgctgaaagt caaggatatt aagtcagcgt actcgaactg gcagattctg  600
aaagaaatcc tgggtaaaat gattaagcaa accaaagcaa gttccggcgt catctggaat  660
agtttcaaag aactggaaga atccgaactg gaaacggtga ttcgtgaaat cccggctccg  720
agttttctga ttccgctgcc gaagcatctg accgcgagca gcagcagcct gctggatcac  780
gaccgcacgg tgtttcagtg gctggatcag caaccgccga gttccgtgct gtatgttagc  840
ttcggtagta cctgggaagt ggatgaaaag gactttctgg aaatcgctcg tggcctggtt  900
gatagcaaac aatctttcct gtgggtggtt cgcccgggtt ttgtgaaggg ctctacgtgg  960
gttgaaccgc tgccggacgg cttcctgggt gaacgtggcc gcattgtcaa atgggtgccg  1020
cagcaagaag tgctggcgca tggcgcgatt ggcgcgtttt ggacccactc cggttggaac  1080
tcaacgctgg aatcggtttg tgaaggtgtc ccgatgattt tctcagattt tggcctggac  1140
cagccgctga atgcacgtta tatgtcggat gttctgaaag tcggtgtgta cctggaaaac  1200
ggttgggaac gcggcgaaat tgcgaatgcc atccgtcgcg ttatggtcga tgaagaaggc  1260
gaatacattc gtcagaatgc tcgcgtcctg aaacaaaagg cggacgtgag cctgatgaaa  1320
```

```
ggcggttcat cgtatgaaag tctggaatcc ctggtttcat acatcagctc tctgtaa     1377

SEQ ID NO: 10          moltype = DNA  length = 1377
FEATURE                Location/Qualifiers
misc_feature           1..1377
                       note = The sequence is synthetized.
source                 1..1377
                       mol_type = other DNA
                       organism = synthetic construct
SEQUENCE: 10
atggaaaata aaaccgaaac caccgtccgc cgtcgtcgcc gtatcattct gttcccggtc  60
ccgttccagg gccacatcaa cccgattctg caactggcga acgtgctgta ttcgaaaggt  120
ttcagcatca ccatcttcca tacgaacttc aacaagccga agaccagcaa ttacccgcac  180
tttacgttcc gttttattct ggataacgac ccgcaggatg aacgcatctc taatctgccg  240
acccacggcc cgctggcggg tatgcgtatt ccgattatca acgaacacgg cgcagatgaa  300
ctgcgtcgcg aactggaact gctgatgctg gccagcgaag aagatgaaga agtttcttgc  360
ctgatcaccg acgcactgtg gtattttgcc cagtctgttg cagatagtct gaacctgcgt  420
cgcctggtcc tgatgaccag cagcctgttc aattttcatg cccacgttag tctgccgcag  480
ttcgatgaac tgggttatct ggacccggat gacaaaaccc gcctggaaga acaggcgagc  540
ggctttccga tgctgaaagt caaggatatt aagtcagcgt actcgaactg gcagattctg  600
aaagaaatcc tgggtaaaat gattaagcaa accaaagcaa gttccggcgt catctggaat  660
agtttcaaag aactggaaga atccgaactg gaaacggtga ttcgtgaaat cccggctccg  720
agttttctga ttccgctgcc gaagcatctg accgcgagca gcagcagcct gctggatcac  780
gaccgcacgg tgtttcagtg gctggatcag caaccgccga gttccgtgct gtatgttagc  840
ttcggtagta cctcggaagt ggatgaaaag gactttctgg aaatcgctcg tggcctggtt  900
gatagcaaac aatctttcct gtgggtggtt cgcccgggtt ttgtgaaggg ctctacgtgg  960
gttgaaccgc tgccggacgg cttcctgggt gaacgtggcc gcattgtcaa atgggtgccg  1020
cagcaagaag tgctggcgca tggcgcgatt ggcgcgtttt ggacccactc cggttggaac  1080
tcaacgctgg aatcggtttg tgaaggtgtc ccgatgattt tctcagattt tccactggac  1140
cagccgctga atgcacgtta tatgtcggat gttctgaaag tcggtgtgta cctggaaaac  1200
ggttgggaac gcggcgaaat tgcgaatgcc atccgtcgcg ttatggtcga tgaagaaggc  1260
gaatacattc gtcagaatgc tcgcgtcctg aaacaaaagg cggacgtgag cctgatgaaa  1320
ggcggttcat cgtatgaaag tctggaatcc ctggtttcat acatcagctc tctgtaa     1377

SEQ ID NO: 11          moltype = DNA  length = 2418
FEATURE                Location/Qualifiers
misc_feature           1..2418
                       note = The sequence is synthetized.
source                 1..2418
                       mol_type = other DNA
                       organism = synthetic construct
SEQUENCE: 11
atggccgaac gtgtcctgac ccgtgtccat agtctgcgtg aacgtgttga tgctaccctg  60
gctgcccacc gtaatgaaat cctgctgttt ctgagtcgta ttgaaagcca cggcaaaggt  120
atcctgaaac cgcacgaact gctggcagaa tttgatgcta ttcgccagga tgacaaaaac  180
aaactgaacg aacatgcatt cgaagaactg ctgaaaagca cccaagaagc tatcgtcctg  240
ccgccgtggg tggcactggc aattcgtctg cgcccgggcg tttgggaata catccgtgtt  300
aacgtcaatg cgctggttgt ggaagaactg agtgtgccgg aatatctgca gtttaaagaa  360
gaactggtcg atggcgcgtc caacggtaat ttcgtgctgg aactggactt tgaaccgttc  420
accgcctcat ttccgaaacc gaccctgacg aaatcgattg gcaacggtgt tgaatttctg  480
aatcgtcatc tgagcgccaa aatgttccac gataaagaat ctatgacccc gctgctggaa  540
tttctgcgcg cacatcacta taaaggtaaa accatgatgc tgaacgatcg tattcagaac  600
agcaatacgc tgcaaaatgt gctgcgcaaa gcggaagaat acctgatcat gctgccgccg  660
gaaaccccgt acttcgaatt tgaacataaa ttccaggaaa ttggcctgga aaaaggctgg  720
ggtgatacgg cagaacgtgt gctggaaatg gtttgcatgc tgctggatct gctggaagct  780
ccggacagct gtaccctgga aaaatttctg ggtcgcattc cgatggtttt caacgtcgtg  840
atcctgtctc cgcacggcta ttttgcgcag gaaaatgtcc tgggttaccc ggataccggc  900
ggtcaggttg tctatattct ggaccaagtg ccggccctgg aacgtgaaat gctgaaacgc  960
atcaaagaac agggcctgga tattatcccg cgtattctga tcgtcacccg tctgctgccg  1020
gacgcagtgg gcaccacgtg cggtcaacgt attgaaaaag tgtatggcgc tgaacattca  1080
cacatcctgc gtgttccgtt tcgcaccgaa aaaggtattg tccgtaaatg gatctcgcgc  1140
tttgaagtgt ggccgtacat ggaaacgttc attgaagatg ttgcaaaaga aatctcagcg  1200
gaactgcagg ccaaaccgga cctgattatc ggcaactata gcgaaggtaa tctggcggcc  1260
tctctgctgg cccataaact gggcgtgacc caatgtacga ttgcacacgc tctggaaaaa  1320
accaaatatc cggattcgga catctactgg aaaaaattcg atgaaaaata ccatttcagc  1380
tctcagttca ccgcagatct gattgctatg aaccacacgg actttattat caccagtacg  1440
ttccaggaaa tcgcgggctc caaagatacc gtgggtcaat acgaaagtca tatggccttt  1500
acgatgccgg gcctgtatcg cgtggttcac ggtatcaacg ttttcgatcc gaaattcaac  1560
attgtctccc cgggtgcaga catcaatctg tatttttcat actcggaaac cgaaaaacgt  1620
ctgacggctt tccatccgga aatcgatgaa ctgctgtata gcgatgtgga aaacgacgaa  1680
cacctgtgcg ttctgaaaga tcgcaccaaa ccgattctgt ttacgatggc gcgtctggac  1740
cgcgttaaaa atctgaccgg cctggtcgaa tggtacgcca aaaacccgcg tctgcgcggt  1800
ctggtgaatc tggtcgtggt tggcggtgat cgtcgcaaag aatctaaaga cctggaagaa  1860
caggcggaaa tgaagaaaat gtacgaactg atcgaaaccc ataacctgaa tggccagttc  1920
cgttggatca gttcccaaat gaaccgtgtt cgcaatggcg aactgtatcg ctacatcgca  1980
gatacgaaag gtgcttttgt ccagccggcg ttttacgaag ccttcggcct gaccgtcgtg  2040
gaagcgatga cgtgcggtct gccgaccttc gcaacgaatc atggcggccc ggcagaaatt  2100
atcgttcacg gcaaaagtgg ttttcatatt gatccgtatc acggcgaaca ggcagctgat  2160
ctgctggccg actttttcga aaaatgtaaa aaagacccgt cacattggga aaccatttcg  2220
```

```
atgggcggtc tgaaacgcat cgaagaaaaa tatacctggc aaatttacag cgaatctctg  2280
ctgacgctgg cggccgtgta cggtttctgg aaacacgttt ctaaactgga tcgtctggaa  2340
attcgtcgct atctggaaat gttttatgcg ctgaaatacc gcaaaatggc ggaagccgtg  2400
ccgctggcag ctgaataa                                                2418

SEQ ID NO: 12          moltype = DNA  length = 2595
FEATURE                Location/Qualifiers
misc_feature           1..2595
                       note = The sequence is synthetized.
source                 1..2595
                       mol_type = other DNA
                       organism = synthetic construct
SEQUENCE: 12
atgagcgcag gagctgattc tccctcaagt caacccttct tggctagccc gcgtggtgtt  60
atcaccccgc gtaccttcac ccgctcgctg tcgttcgcag gcggtacgcc gtccgaaatt  120
ttgaaggcgg gcttggttca cagccgtaat gagctggtgc tgctgttcag ccgttgcatg  180
gcaaagagca aagcggacaa gccaattctg ttaccgcata ttattatgga tgagttatgc  240
gccgtgtgtg atgaatgcaa taatccgatg ctgaaatctg gtgagatcgc ggcgatcttg  300
aaaaccgttc aggaagcggt agttatcgca ccgcgaatcg ccttcgcgtt gagacctacg  360
atgggtgaat ggtactacgt tcgcgtgtct gttgaagata tgcgcgttga agaaatgacc  420
gctgcgcact atctcgcgtt taaagagaag ctggttccac tggaccaaga tcgtcacggc  480
tacgacccat tcgtgctgga gctggacttg aagccgtttg gcgcacacca gcctaagatt  540
agcctgcaaa gccacatcgg taacggtgtt agcttcctga atcgcacgct gtcggcgaaa  600
atgttttccc agaacgccaa tgcggaaggc agccaattga tgttggactt cctgcgtgaa  660
tttaagcacg gaggcgaaaa gttactgcta agcccgcgtg tgaatagcgt gcagaaattg  720
cgccactcac tgctgcgtgc tgaccgctta ctggagaagc acgaagacga ggacccgctg  780
tctgttgtgc aaggtatcga cgagctgggc ttcctgccgg gttggggtaa cactgttggc  840
cgtgttagag agtcctttca gctgctgttg gacatcatcc aggcaccaga cgctgatact  900
ctggaaaagt tcctggcccg cttgccgctg atggttaaag ttgtcatctt gtcgccgcat  960
ggttatttcg gtcaaaccaa tgtgttgggt atgccggaca ccggtggtca ggtggtctac  1020
attctggacc aggttcgtgc gatggagcgt gagatgcagc agcgtctaga tgaagcgggc  1080
cttcagaatg tgaaagcgga tgttgttgtg ctgacccgtc tgattccgga tgcacatggt  1140
acttcctgca acgagcgctt ggagccgatt agtggctgcc aaaacgcgcg tatcctgcgt  1200
gttccgtttc gggatagcga aggtcgtatc ctgaatcatt gggtttccag gttcgatctg  1260
tggccgtatc tggagcgctt taccattgac gccacgaagg aaatcctggc tgaaatgggc  1320
ggtaaaccgg acttcattat cggcaactat agcgatggta acttagtggc gaccctcatg  1380
agccatcgta tgaacgtgac ccagtgtaac attgcgcatg cgctggaaaa aaccaaatac  1440
gatgatgccg acatttactg gcagaagctt gaagacaaat accattttag ctgccaattt  1500
acggccgacc tgatcgcaat gaactctgcg gattttatcg tcacctccac ctaccaggag  1560
atcgctggtc atgaggaaat ggtgggccaa tatgagagct ataagagctt taccatgcca  1620
cagctgtacc gcgttgtgga gggcattgac atctacaacc cgaagttcaa cattgtgagc  1680
ccgggtgcgg acctggacat ctactttccg taccaggaga aggagaggcg tttgaccggc  1740
ctgcataagg acattgaagc gctgctgttt gacccggatt ttaaaggtac ggtcggtcag  1800
ttagaggaca gagacaaacc gatcctgttt tctatggcgc gtttggacaa agtgaagaac  1860
ctgactggcc tggccgagtg gtacgcgggc aatcagcgtt tgcgtggtct ggtcaacctg  1920
gtcatagtcg gtggcgttat tgatccggct gctacgatgg accgcgaaga ggcagcggag  1980
tgcgaacaca tgcacgaact tgtcgagaag tataaaatgc atggcacgtt ccgctggatt  2040
gttgctcaga agaaccgtgt acgtaacggc gagctgtata gatacatcgc tgatactcgt  2100
ggtgctttcg cccaaccggc actgtacgaa gcctttgggc tgaccgtgat cgaggcgatg  2160
acctgtggtc ttccgacctt cgcaaccaac cacggcggtc cgtccgaaat cattaaacac  2220
aagaaaagcg gcttccatat cgacccgtat cacggtgcgg aagcggcgga tctgatggcg  2280
gatttctttg aacgttctca aaaggagccg tctcattgga ccaagatctc cgaggcggcg  2340
caagaacgta tttttagccg ttacacgtgg tcaatctacg caaagcgcct ggtgaccttg  2400
agccacgtgt ataccttctg gaaacacgtg accagcctgg agagccgcga aaccaaacgt  2460
tatctggaga tgttctatat tctgcaaatg cgtaaattgg tagccaaaat gtcggaagag  2520
accgtggaaa aggagaaggc ggcggcagag gcaggtccgg cgggcccgcc taaagttggc  2580
tttggtgcta tgtaa                                                   2595

SEQ ID NO: 13          moltype = DNA  length = 36
FEATURE                Location/Qualifiers
misc_feature           1..36
                       note = The sequence is synthetized.
source                 1..36
                       mol_type = other DNA
                       organism = synthetic construct
SEQUENCE: 13
ccgctggcgg acatgcgtat tccgattatc aacgaa                            36

SEQ ID NO: 14          moltype = DNA  length = 36
FEATURE                Location/Qualifiers
misc_feature           1..36
                       note = The sequence is synthetized.
source                 1..36
                       mol_type = other DNA
                       organism = synthetic construct
SEQUENCE: 14
aatacgcatg tccgccagcg ggccgtgggt cggcag                            36

SEQ ID NO: 15          moltype = DNA  length = 36
```

```
FEATURE                Location/Qualifiers
misc_feature           1..36
                       note = The sequence is synthetized.
source                 1..36
                       mol_type = other DNA
                       organism = synthetic construct
SEQUENCE: 15
ctgatgaccg acagcctgtt caattttcat gcccac                              36

SEQ ID NO: 16          moltype = DNA  length = 36
FEATURE                Location/Qualifiers
misc_feature           1..36
                       note = The sequence is synthetized.
source                 1..36
                       mol_type = other DNA
                       organism = synthetic construct
SEQUENCE: 16
gaacaggctg tcggtcatca ggaccaggcg acgcag                              36

SEQ ID NO: 17          moltype = DNA  length = 36
FEATURE                Location/Qualifiers
misc_feature           1..36
                       note = The sequence is synthetized.
source                 1..36
                       mol_type = other DNA
                       organism = synthetic construct
SEQUENCE: 17
ctgatgacca acagcctgtt caattttcat gcccac                              36

SEQ ID NO: 18          moltype = DNA  length = 36
FEATURE                Location/Qualifiers
misc_feature           1..36
                       note = The sequence is synthetized.
source                 1..36
                       mol_type = other DNA
                       organism = synthetic construct
SEQUENCE: 18
gaacaggctg ttggtcatca ggaccaggcg acgcag                              36

SEQ ID NO: 19          moltype = DNA  length = 36
FEATURE                Location/Qualifiers
misc_feature           1..36
                       note = The sequence is synthetized.
source                 1..36
                       mol_type = other DNA
                       organism = synthetic construct
SEQUENCE: 19
tcagcgtacc aaaactggca gattctgaaa gaaatc                              36

SEQ ID NO: 20          moltype = DNA  length = 36
FEATURE                Location/Qualifiers
misc_feature           1..36
                       note = The sequence is synthetized.
source                 1..36
                       mol_type = other DNA
                       organism = synthetic construct
SEQUENCE: 20
ctgccagttt tggtacgctg acttaatatc cttgac                              36

SEQ ID NO: 21          moltype = DNA  length = 36
FEATURE                Location/Qualifiers
misc_feature           1..36
                       note = The sequence is synthetized.
source                 1..36
                       mol_type = other DNA
                       organism = synthetic construct
SEQUENCE: 21
tggcagattt acaaagaaat cctgggtaaa atgatt                              36

SEQ ID NO: 22          moltype = DNA  length = 36
FEATURE                Location/Qualifiers
misc_feature           1..36
                       note = The sequence is synthetized.
source                 1..36
                       mol_type = other DNA
                       organism = synthetic construct
SEQUENCE: 22
gatttctttg taaatctgcc agttcgagta cgctga                              36
```

-continued

```
SEQ ID NO: 23           moltype = DNA  length = 36
FEATURE                 Location/Qualifiers
misc_feature            1..36
                        note = The sequence is synthetized.
source                  1..36
                        mol_type = other DNA
                        organism = synthetic construct
SEQUENCE: 23
ttcggtagta gctcggaagt ggatgaaaag gacttt                        36

SEQ ID NO: 24           moltype = DNA  length = 36
FEATURE                 Location/Qualifiers
misc_feature            1..36
                        note = The sequence is synthetized.
source                  1..36
                        mol_type = other DNA
                        organism = synthetic construct
SEQUENCE: 24
cacttccgag ctactaccga agctaacata cagcac                        36

SEQ ID NO: 25           moltype = DNA  length = 36
FEATURE                 Location/Qualifiers
misc_feature            1..36
                        note = The sequence is synthetized.
source                  1..36
                        mol_type = other DNA
                        organism = synthetic construct
SEQUENCE: 25
ggtagtacct gggaagtgga tgaaaaggac tttctg                        36

SEQ ID NO: 26           moltype = DNA  length = 36
FEATURE                 Location/Qualifiers
misc_feature            1..36
                        note = The sequence is synthetized.
source                  1..36
                        mol_type = other DNA
                        organism = synthetic construct
SEQUENCE: 26
atccacttcc caggtactac cgaagctaac atacag                        36

SEQ ID NO: 27           moltype = DNA  length = 36
FEATURE                 Location/Qualifiers
misc_feature            1..36
                        note = The sequence is synthetized.
source                  1..36
                        mol_type = other DNA
                        organism = synthetic construct
SEQUENCE: 27
tcagattttc cactggacca gccgctgaat gcacgt                        36

SEQ ID NO: 28           moltype = DNA  length = 36
FEATURE                 Location/Qualifiers
misc_feature            1..36
                        note = The sequence is synthetized.
source                  1..36
                        mol_type = other DNA
                        organism = synthetic construct
SEQUENCE: 28
ctggtccagt ggaaaatctg agaaaatcat cgggac                        36
```